United States Patent [19]
Athanasiou et al.

[11] Patent Number: 6,013,853
[45] Date of Patent: Jan. 11, 2000

[54] CONTINUOUS RELEASE POLYMERIC IMPLANT CARRIER

[75] Inventors: Kyriacos A Athanasiou; Barbara D Boyan, both of San Antonio, Tex.

[73] Assignee: The University of Texas System, Austin, Tex.

[21] Appl. No.: 08/196,970

[22] Filed: Feb. 15, 1994

Related U.S. Application Data

[63] Continuation-in-part of application No. 08/123,812, Sep. 20, 1993, Pat. No. 5,607,474, which is a continuation of application No. 07/837,401, Feb. 14, 1992, abandoned.

[51] Int. Cl.[7] .................................. A61F 2/02; A61F 2/28
[52] U.S. Cl. .................................. 623/11; 623/16; 623/66
[58] Field of Search .................................. 623/1, 11, 12, 623/13, 15, 16, 18, 66; 604/891.1; 424/422, 426, 78; 435/284, 240

[56] References Cited

U.S. PATENT DOCUMENTS

| | | |
|---|---|---|
| 3,620,218 | 11/1971 | Schmitt . |
| 3,739,773 | 6/1973 | Schmitt . |
| 3,755,558 | 8/1973 | Scribner .................................. 424/47 |
| 3,773,919 | 11/1973 | Boswell et al. .................................. 248/558 |
| 3,887,699 | 6/1975 | Yolles .................................. 424/19 |
| 3,976,071 | 8/1976 | Sadek .................................. 128/260 |
| 3,991,766 | 11/1976 | Schmitt et al. .................................. 128/335.5 |
| 4,011,312 | 3/1977 | Reuter et al. .................................. 424/78 |
| 4,048,256 | 9/1977 | Casey et al. .................................. 260/860 |
| 4,076,798 | 2/1978 | Casey et al. .................................. 424/22 |
| 4,095,600 | 6/1978 | Casey et al. .................................. 128/335.5 |
| 4,118,470 | 10/1978 | Casey et al. .................................. 424/19 |
| 4,122,129 | 10/1978 | Casey et al. .................................. 260/860 |
| 4,261,969 | 4/1981 | Heller . |
| 4,293,539 | 10/1981 | Ludwig et al. .................................. 424/19 |
| 4,346,709 | 8/1982 | Schmitt .................................. 128/260 |
| 4,460,562 | 7/1984 | Keith . |
| 4,532,123 | 7/1985 | Gardner . |
| 4,553,272 | 11/1985 | Mears .................................. 623/16 |

(List continued on next page.)

FOREIGN PATENT DOCUMENTS

| | | |
|---|---|---|
| WO 88/03417 | 5/1988 | European Pat. Off. . |
| 0 277 678 | 8/1988 | European Pat. Off. . |
| 0 326 426 | 8/1989 | European Pat. Off. . |
| 0 473 268 A2 | 3/1992 | European Pat. Off. . |
| 1 745 676 | 7/1970 | Germany . |
| 2 209 937 | 6/1989 | United Kingdom . |
| 2 234 896 | 2/1991 | United Kingdom . |

(List continued on next page.)

OTHER PUBLICATIONS

Akizuki, S. et al., "Tensile Properties of Human Knee Joint Cartilage. II. Correlations Between Weight Bearing and Tissue Pathology and the Kinetics of Swelling", *J. Orthopaedic Res.* (1987) 5:173–186.

Alper, J., "Will bone morphogenic proteins pay off?", *Bio/Technology* (1993) 11:649–651.

Armstrong, C.G. and Mow, V.C., "Variations in the Intrinsic Mechanical Properties of Human Articular Cartilage with Age, Degeneration, and Water Content", *Bone and Joint Surg.* (1982) 64–A:88–94.

Athanasiou, K. et al., "Use of Biodegradable Implants for Repairing Large Articular Cartilage Defects in the Rabbit," *Proc. 38th Ann. Mtg. Ortho. Res. Soc.* Feb. 18, 1992.

(List continued on next page.)

*Primary Examiner*—David Isabella
*Attorney, Agent, or Firm*—Greenlee, Winner and Sullivan, P.C.

[57] ABSTRACT

Biodegradable, porous, polymeric implant material provides substantially continuous release of bioactive agent during in vivo use. Bioactive agent is initially released in amounts that are less than degradation rate of polymer, thereby promoting migration of cells into material. Later larger amounts of bioactive agent is released, thereby promoting differentiation of cells. Method of making material includes step of applying vacuum to form pores. Implant material may be adapted for one phase implant (e.g., for bone or cartilage) or for two phase layered implant (e.g., for cartilage layer on top of bone layer).

36 Claims, 5 Drawing Sheets

U.S. PATENT DOCUMENTS

| | | | |
|---|---|---|---|
| 4,622,244 | 11/1986 | Lapka et al. | 427/213 |
| 4,650,488 | 3/1987 | Bays et al. | 623/12 |
| 4,652,264 | 3/1987 | Dumican . | |
| 4,705,039 | 11/1987 | Sakaguchi . | |
| 4,756,862 | 7/1988 | Spector . | |
| 4,767,628 | 8/1988 | Hutchinson | 424/426 |
| 4,801,739 | 1/1989 | Franz et al. | 560/185 |
| 4,818,542 | 4/1989 | DeLuca et al. | 424/491 |
| 4,832,686 | 5/1989 | Anderson | 604/49 |
| 4,874,388 | 10/1989 | Wong et al. | 604/891.1 |
| 4,883,666 | 11/1989 | Sabel et al. | 424/422 |
| 4,886,870 | 12/1989 | D'Amore et al. | 623/15 |
| 4,897,268 | 1/1990 | Tice et al. | 424/422 |
| 4,947,840 | 8/1990 | Yannas et al. | 623/15 |
| 4,962,091 | 10/1990 | Eppstein et al. | 514/2 |
| 4,963,489 | 10/1990 | Naughton et al. | 435/240 |
| 4,968,317 | 11/1990 | Törmälä et al. | 606/77 |
| 4,997,440 | 3/1991 | Dumican | 623/1 |
| 5,004,602 | 4/1991 | Hutchinson | 424/78 |
| 5,032,508 | 7/1991 | Naughton et al. | 435/32 |
| 5,041,138 | 8/1991 | Vacanti et al. | 623/16 |
| 5,053,050 | 10/1991 | Itay | 623/16 |
| 5,084,051 | 1/1992 | Tormala . | |
| 5,100,668 | 3/1992 | Edelman et al. | 424/422 |
| 5,134,122 | 7/1992 | Orsolini | 514/15 |
| 5,152,791 | 10/1992 | Hakamatsuka . | |
| 5,160,490 | 11/1992 | Naughton et al. | 435/284 |
| 5,206,023 | 4/1993 | Hunziker | 424/423 |
| 5,270,300 | 12/1993 | Hunziker | 514/12 |
| 5,286,763 | 2/1994 | Gerhart et al. | 604/891.1 |
| 5,290,271 | 3/1994 | Jernberg | 604/891.1 |
| 5,342,348 | 8/1994 | Kaplan | 604/891.1 |
| 5,464,440 | 11/1995 | Johansson | 623/15 |
| 5,492,697 | 2/1996 | Boyan et al. | 623/11 |

FOREIGN PATENT DOCUMENTS

| | | |
|---|---|---|
| WO 86/00526 | 1/1986 | WIPO . |
| WO 87/00059 | 1/1987 | WIPO . |
| WO 91/09079 | 6/1991 | WIPO . |
| WO 92/11843 | 7/1992 | WIPO . |
| WO 92/11844 | 7/1992 | WIPO . |
| WO 92/14749 | 9/1992 | WIPO . |
| PCT/US93/01315 | 5/1993 | WIPO . |
| WO 93/15694 | 8/1993 | WIPO . |
| WO 93/15767 | 8/1993 | WIPO . |

OTHER PUBLICATIONS

Beck, L.R. and Pope, V.Z., "Controlled–Release Delivery Systems for Hormones, A Review of their Properties and Current Therapeutic Use", *Drugs* (1984) 27:528–547.

Cohen, S. et al., "Controlled Delivery Systems for Proteins Based on Poly(Lactic/Glycolic Acid) Microspheres", Proceed Int. Symp. Control. Rel. Bioact. Mater., (1991) *Controlled Release Soc., Inc.* 18:101–102.

Cutright, D.E. et al., "Degradation rates of polymers and copolymers of polylactic and polyglycolic acids", *Oral Surg.* (Jan. 1974) 37(1):142–152.

Edelman, E.R. et al., "Controlled and modulated release of basic fibroblast growth factor," *Biomaterials* (1991) 12(7):619–626.

Edelman, E.R. and Nugert, M.A., "Controlled Release of Basic Fibroblast Growth Factor", *DN&P* (1991) 4(6):352–357.

Freed, L. et al., "Neocartilage formation in vitro and in vivo using cells cultured on synthetic biodegradable polymers", *J. Biomed. Materials Res.* (1993) 27:11–23.

Fung, Y.C., "Biomechanics: Mechanical Properties of Living Tissues", *Springer–Verlag New York* (1981) 384–385.

Gilding, D.K. et al., "Biodegradable polymers for use in surgery–polyglycolic/poly(actic acid) homo–and copolymers: 1", *Polymer* (1979) 20:1459–1464.

Gilding, D.K., "Degradation of Polymers: Mechanisms and Implications for Biomedical Applications", *Fundamental Aspects of Biocompatibility,* Chapter 3, pp. 43–65.

Heckman, J.D., et al., "The Use of Bone Morphogenetic Protein in the Treatment of Non–Union in a Canine Model", *J. Bone and Joint Surg.* (1991) 73–A:750–764.

Heller, J., "Biodegradable Polymers in Controlled Drug Delivery", *CRC Critical Reviews in Therapeutic Drug Carrier Systems* (1985) 1(1):39–90.

Heller, J., "Development of poly(ortho esters): a historical overview", *Biomaterials* (1990) 1(1):659–665.

Hollinger, J., "Factors for Osseous Repair and Delivery: Part II", *J. Craniofacial Surg.* (1993) 4(3):135–141.

Hollinger, J. and Chaudhari, A., "Bone Regeneration Materials for the Mandibular and Craniofacial Complex", *Cells and Materials* (1992) 2(2):143–151.

Hollinger, J.O. et al., "Osseous wound healing with xenogeneic bone implants with a biodegradable carrier", *Surgery* (Jan. 1990) 50–54.

Jacob, E. et al., "Evaluation of Biodegradable Ampicillin Anhydrate Microcapsules for Local Treatment of Experimental *Staphylococcal Osteomyelitis",* Clinical Orthopaedics and Related Research (M.R. Urist, ed.), J.B. Lippincott Company, Philadelphia, (1989) 237–244.

Kleinschmidt, J.C. et al., "A Multiphase System Bone Implant for Regenerating the Calvaria", *Plastic and Reconstructive Surgery* (Apr. 1993) 91(4):581–588.

Langer, R., "Controlled Release: A New Approach to Drug Delivery", *Technology Review* (Apr. 1981) 26–34.

Langer, R., "New Methods of Drug Delivery", Science (Sep. 28, 1990) *Articles* 249:1527–1533.

Langer, R. and Vacanti, J.P., "Tissue Engineering", *Science* (May 14, 1993) 260:920–926.

Lewis, D.H., "Controlled Release of Bioactive Agents from Lactide/Glycolide Polymers", Biodegradable Polymers as Drug Delivery Systems (M. Chasin and R. Langer, eds). *Marcel Dekker, Inc.* New York (1990) 1–.

Lucas, P.A. et al., "Ectopic induction of cartilage and bone by water–soluble proteins from bovine bone using a polyanhydride delivery vehicle", *J. Biomed. Materials Res.* (1990) 24:901–911.

Masters, D.B. et al., "Prolonged Regional Nerve Blockade by Controlled Release of Local Anesthetic from a Biodegradable Polymer Matrix", *Anesthesiology* (1993) 79:340–346.

Mathiowitz, E. et al., "Polyanhydride Microspheres as Drug Carriers. II. Microencapsulation by Solvent Removal", *J. App. Polymer Sci.* (1988) 35:755–774.

Mow, V.C. et al., "Biphasic Creep and Stress Relaxation of Articular Cartilage in Compression: Theory and Experiments", *J. of Biomechanical Eng.* (Feb. 1980) 102:73–83.

Reed, A.M. et al., "Biodegradable polymers for use in surgery—poly(glycolic)/poly(lactic acid) homo and copolymers: 2. In vitro degradation", *Polymer* (1981) 22:494–498.

Reilly, D.T. et al., "The Elastic Modulus for Bone", *J. Biomechanics* (1974) 7:271–275.

Reilly, D.T. and Burstein, A.H., "The Mechanical Properties of Cortical Bone," *J. Bone and Joint Surg.* (1974) 56–A(5):1001–1022.

Rosilio, V. et al., "A physicochemical study of the morphology of progesterone–loaded microspheres fabricated from poly (D,L–lactide–co–glycolide)", *J. Biomed. Materials Res.* (1991) 25:667–682.

Sanders, L.M. et al., "Prolonged Controlled–Release of Nafarelin, a Luteinizing Hormone–Releasing Hormone Analogue, From Biodegradable Polymeric Implants: Influence of Composition and Molecular Weight of Polymer", *J. Pharm. Sci.* (1986) 75(4):356–360.

Schakenraad, J.M. et al. "Biodegradable hollow fibres for the controlled release of drugs", *Biomaterials* (1988) 9:116–120.

Schwope, A.D. et al., "Development of Polylactic/Glycolic Acid Delivery Systems for Use in Treatment of Narcotic Addiction"; Natl Inst. on Drug Abuse Research Monograph Series 4, Narcotic Adjustments: *The Search for Long–Acting Preparations* (1975) 13–18.

Silberstein, G.B. and Daniel, C.W., "Reversible Inhibition of Mammary Gland Growth by Transforming Growth Factor–$\beta$", *Science* (1987) 237:291–293.

Spilker, R.L. and Suh, Jun–Kyo, "Effects of Friction on the Unconfined Compressive Response of Articular Cartilage: A Finite Element Analysis," *J. Biomechanical Eng.* (May 1990) 112:138–146.

Stoeckemann, K. and Sandow, J., "Effects of the luteinizing–hormone–releasing hormone (LHRH) antagonist ramorelix (hoe013) and the LHRH agonist buserelin on demethylbenz[a]anthracene–induced mammary carcinoma: studies with slow–release formulations," *J. Cancer Res. Clin. Oncol.* (1993) 119:457–462.

Tencer, A.F., et al., "The effect of local controlled release of sodium fluoride on the stimulation of bone growth", *J. Biomed. Material Res.* (1989) 23:571–589.

Toriumi, D.M. et al., "Mandibular Reconstruction with a Recombinant Bone–Inducing Factor: Functional and Biomechanical Evaluation," *Arch Otolaryngol Head Neck Surg.* (Oct. 1991) 117:1101–1112.

Vacanti, C.A. et al., "Tissue–Engineered Growth of Bone and Cartilage", *Transplanation Proceedings* (Feb. 1993) 25(1):1019–1021.

Wang, H.T. et al., "Degradation of poly(ester) microspheres", *Biomaterials* (Nov. 1990) 11:679–685.

Williams, D.F., "Some Observations on the Role of Cellular Enzymes in the In–Vivo Degradation of Polymers", Materials (B.C. Syreti and A. Acharya, eds.), *American Soc. for Testing and Materials,* Philadelphia, PA, (1979).

Woo, S.L., "Mechanical Properties of Tendons and Ligaments", 4th Internat'l Congress of Biorheology, Symposium on Mechanical Properties of Living Tissues, *Biorheology* (1982) 19:385–396.

Woo, S.L. et al., "The Biomechanical and Morphological Changes in the Medial Collateral Ligament of the Rabbit after Immobilization and Remobilization", *J. Bone and Joint Surg.* (1987) 69–A:1200–1211.

Yamakawa, I. et al., "Controlled Release of Insulin from Plasma–Irradiated Sandwitch Device Using Poly–DL–lactic Acid," *Biol. Pharm. Bull* (1993) 16(2):182–187.

Wang, H.T. et al. (1991) "Influence of formulation methods on the in vitro controlled release of protein from poly(ester) microspheres", *Polymers for Cosmetic and Pharmaceutical Applications,* Plenum, New York, pp. 23–31.

Robert Langler, "Controlled Release: A New Approach to Drug Delivery", Technology Review, pp. 26–34, Apr. 1981.

D.F. Williams, "Some Observations on the Role of Cellular Enzymes in the In–Vivo Degradation of Polymers," Corrosion and Degradation of Implant Materials, ASTM STP, 684 B.C. Syrett and A. Acharya, Eds., American Society for Testing and Materials, 1979, pp. 61–75.

English Translation of French Patent No. 2,612,392.

CONTINUOUS RELEASE POLYMERIC IMPLANT CARRIER

CROSS-REFERENCE TO RELATED APPLICATIONS

This application is a continuation-in-part of U.S. Ser. No. 08/123,812 filed Sep. 20, 1993 now U.S. Pat. No. 5,607,474, which is a continuation of Ser. No. 07/837,401 filed Feb. 14, 1992 now abandoned, both of which are fully incorporated herein by reference.

FIELD OF THE INVENTION

This invention is in the field of biodegradable polymeric tissue implant materials used as carriers for bioactive agents. In a preferred embodiment, the implants of this invention provide a smooth, continuous release profile for such agents, and are especially useful for delivering growth factors for enhancing healing of bone and cartilage tissue.

BACKGROUND OF THE INVENTION

The use of biodegradable or bioerodible polymers to provide sustained or controlled release of drugs or other hormones has been known since the 1960s. (Langer, R. (April, 1981) "Controlled Release: A New Approach to Drug Delivery," Technology Review 26–34.) Biodegradable implants for the controlled release of hormones, particularly contraceptive hormones, were developed in the 1970s. (Beck, L. R. and Pope, V. Z. (1984), "Controlled-Release Delivery Systems for Hormones," Drugs 27:528–547.)

A number of biodegradable polymers have been used for controlled release of drugs including polyanhydrides (Mathiowitz, E., et al. (1988), "Polyanhydride Microspheres as Drug Carriers," J. Appl. Polymer Science 35:755–774; Lucas, P.A. et al. (1990), "Ectopic induction of cartilage and bone by water-soluble proteins from bovine bone using a polyanhydride delivery vehicle," J. Biomed. Materials Res. 24:901–911; Masters, D. B., et al. (1993), "Prolonged Regional Nerve Blockade by Controlled Release of Local Anesthetic from a Biodegradable Polymer Matrix," Anesthesiology 79:340–346); and poly(ortho esters) (Heller, J (1990), "Development of poly(ortho esters): a historical overview," Biomaterials 11:659–665).

Aliphatic polyesters comprise another important class of biodegradable polymers. Polymers of polylactic acid (PLA) and polyglycolic acid (PGA) have been used as biodegradable implants for tissue repair for several decades. (See, e.g. Cutright, D. E., et al. (1974), "Degradation rates of polymers and copolymers of polylactic and polyglycolic acids," Oral Surg. 37:142–152; and Gilding, D. K. and Reed, A. M. (1979), "Biodegradable polymers for use in surgery— polyglycolic/polylactic acid homo-and copolymers:1," Polymer 20:1459–1464.)

It has been found that degradation of polyglycolic acid may take place at essentially the same rate in vivo as in vitro. Schwope, A. D., et al. (1975), "Development of Polylactic/ glycolic Acid Delivery Systems for Use in Treatment of Narcotic Addiction," Nat'l Inst. Drug Abuse Res. Monogr. Ser. 4:13–18, appears to disclose that $\frac{1}{16}$" diameter beads and rods made from PLA/PGA copolymers to which naltrexone was added by dissolving the polymer and drug in a common solvent and casting, released the drug at the same rate in vivo as in vitro. Drug release in both cases appears to occur by essentially the same mechanism in vivo as in vitro, that is, by hydrolysis in an aqueous environment, and although one report appears to indicate that in the in vivo environment initiation of the degradation process is enhanced (Williams, D. F. (1979), "Some Observations on the Role of Cellular Enzymes in the In-Vivo Degradation of Polymers," in Corrosion and Degradation of Implant Materials, ASTM STP 684, Syrett, B. C. and Acharya, A., eds., American Soc. for Testing and Materials 61–75), later reports appear to indicate that the in vivo degradation rate may be simulated in vitro using phosphate buffer solution. (Gilding, D. K. (1981), "Degradation of Polymers: Mechanisms and Implications for Biomedical Applications," In: Williams, D. F. ed. Fundamental aspects of biocompatibility," CRC Press, 44–65.) Macroscopic devices such as cylinders about 3×20 mm of polylactic acid and polyglycolic acid copolymers may degrade at the same rate in vivo as in vitro and cleavage may be due to simple hydrolysis with no enzymatic contributions. (Heller, J. (1984), "Biodegradable Polymers in Controlled Drug Delivery," Critical Reviews in Therapeutic Drug Carrier Systems, 1(1):39–90.)

Aliphatic polyesters such as polymers based on lactic acid, glycolic acid and their copolymers appear to degrade by a bulk erosion process, so that rate of drug release from monolithic devices may not be either linear or predictable. (Heller, J. (1984), "Biodegradable Polymers in Controlled Drug Delivery," Critical Reviews in Therapeutic Drug Carrier Systems, 1(1) :39–90.) These copolymers displaying bulk or homogenous erosion may display significant degradation in the matrix interior, which may result in "dose-dumping" in contrast to surface eroding systems such as those composed of polyanhydrides. (Langer, R. (1990), "New Methods of Drug Delivery," Science 249:1527–1533.)

50:50 glycolic acid:lactic acid copolymers appear to be described as inherently hydrophilic and useful for release of more hydrophobic drugs. (Reed, A. M. and Gilding, D. K. (1981), "Biodegradable polymers for use in surgery—poly (glycolic)/poly(lactic acid) homo and copolymers: 2. In vitro degradation," Polymer 22:494–498.)

A number of controlled release formulations appear to have been made using polylactic/polyglycolic acid copolymers in the form of microparticles or microspheres. U.S. Pat. No. 3,773,919 to Albert, et al. issued Nov. 20, 1973 for "Polylactic-Drug Mixtures" appears to describe various methods for incorporating drugs into the polymer e.g. by coating, mixing the drug with melted polymer, or mixing with a common solvent and drying to form a film or powder. U.S. Pat. No. 4,622,244 to Lapka issued Nov. 11, 1986 for "Process for Preparation of Microcapsules" appears to disclose a process for preparing microspheres comprising active substances coated with polymer useful for injection. U.S. Pat. No. 4,818,542 to DeLuca et al. issued Apr. 4, 1989 "Porous Microspheres for Drug Delivery and Methods for Making Same" appears to disclose polymeric microspheres made with pores in which drugs are incorporated. U.S. Pat. No. 4,897,268 to Tice et al. issued Jan. 30, 1990 for "Drug Delivery System and Method of Making the Same" appears to describe the use of polymers degrading at different rates to form microcapsules for controlled release of active ingredients. U.K. Patent Application 2 234 896 A to Sandoz, Ltd. published Feb. 20, 1991 for "Delayed Release Formulations" appears to describe microparticles formed by a process in which the drug and polymer are dissolved in different phases. Rosilio, V. et al. (1991), "A physiochemical study of the morphology of progesterone-loaded microspheres fabricated from poly(D,L-lactide-co-glycolide)," J. Biomed. Materials Res. 25:667–682 appears to describe progesterone-loaded microspheres of polylactic acid, polyglycolic acid copolymer.

Studies of such microspheres reveal that proteins carried therein may be released before the polymer itself is degraded. (Wang, H. T., et al. (1990), "Degradation of poly(ester) microspheres," Biomaterials 11:679–685.) Nevertheless, microencapsulation with polylactic/ polyglycolic copolymer does appear to slow down diffusion of locally administered antibiotics. (Jacob, E., et al. (1991), "Evaluation of Biodegradable Ampicillin Anhydrate Microcapsules for Local Treatment of Experimental Staphylococcal Osteomyelitis," Clin. Orthopaedics and Related Research 267:237–244.) Microspheres made of 75/25 polylactic/polyglycolic acid copolymers and molecular weights of 14 kDa or less appear to have released proteins over a four to six week period. (Cohen, S., et al. (1991), "Controlled Delivery Systems for Proteins Based on Poly (lactic/Glycolic acid) Microspheres," Proceed. Intern. Sympo. Control. Rel. Bioact. Mater. 18:101–102.)

Efforts have been made to improve the predictability of drug release from PGA/PLA microspheres. PCT Publication WO 91/09079 published Jun. 27, 1991 by Farmitalia Carlo Erba S.R.L. for "Use of Supercritical Fluids to Obtain Porous Sponges of Biodegradable Polymers" appears to describe the use of supercritical fluids to manufacture porous microspheres for drug delivery. PCT Publication WO 92/11844 published Jul. 23, 1992 by Enzytech, Inc. for "Stabilization of Proteins by Cationic Biopolymers" appears to describe a method for incorporation of proteins in the form of specific noncovalent complexes with polycationic reagents into sustained release systems which are polymeric microcapsules.

Delivery forms other than microspheres utilizing polylactic acid and polyglycolic acid polymers also appear to have been formulated. U.S. Pat. No. 3,755,558 to Scribner, issued Aug. 28, 1973 for "Polylactide-Drug Mixtures for Topical Application," appears to disclose the preparation of polylactic acid films with active ingredients incorporated therein. A number of methods for incorporation of the active ingredient into the polymer (as described above with respect to U.S. Pat. No. 3,773,919) also appear to have been taught. U.S. Pat. No. 3,887,699 to Yolles issued Jun. 3, 1975 for "Biodegradable Polymeric Article for Dispensing Drugs," appears to disclose the use of shaped polymeric articles such as films, hollow tubing, spheroids useful for injection or oral ingestion, or solid "spaghetti-like" or "fiber-like" configurations for controlled release of drugs wherein the device exudes the drug to the surface of the article. One method of mixing a drug with the polymer is to dissolve both in a suitable solvent, drive off solvent and mold the residue. Large implants and high molecular weight proteins do not appear to be taught as components of the invention described therein. U.S. Pat. No. 3,991,766 to Schmitt et al. issued Nov. 17, 1976 for "Controlled Release of Medicaments using Polymers from Glycolic Acid," appears to disclose filaments comprising PGA and antibiotics. No large proteins appear to be disclosed nor do release kinetics appear to be provided.

U.S. Pat. No. 4,118,470 to Casey et al. issued Oct. 3, 1978 for "Normally-solid, Bioabsorbable, Hydrolyzable, Polymeric Reaction Product," appears to disclose polymeric films for drug delivery. Hollow fibers of polylactic acid polymers also appear to have been described. (Schakenraad, J. M., et al. (1988), "Biodegradable hollow fibres for the controlled release of drugs," Biomaterials 9:116–120.) U.S. Pat. No. 4,801,739 to Franz et al. issued Jan. 31, 1989 for "Oligomeric Hydroxycarboxylic Acid Derivatives, Their Production and Use," appears to disclose polylactic/ polyglycolic acid copolymers partially in the form of amides or esters with a sterol as carriers for active ingredients in the form of microparticles, 1 mm rods and films.

U.K. Patent Application No. 2 209 937 A published Jun. 1, 1989 appears to disclose the use of ground polymers as continuous drug release agents. U.S. Pat. No. 4,883,666 to Sabel et al. issued Nov. 28, 1989 for "Controlled Drug Delivery System for Treatment of Neural Disorders," appears to disclose the use of 3 mm diameter discs with pinholes therein for linear release of drugs. U.S. Pat. No. 4,962,091 to Eppstein et al. issued Oct. 9, 1990 for "Controlled Release of Macromolecular Polypeptides" appears to disclose polylactic acid/polyglycolic acid copolymeric films and coated wires which release growth factors including TGF-$\beta$ over a period of up to 100 days. The polymers appear to comprise a micro-suspension of polypeptide and other water-soluble components in which the particles have a diameter of 10 microns or less. EPO Patent Application No. 0 473 268 A2 published Mar. 4, 1992 by Imperial Chemical Industries, PLC appears to disclose the use of 1 mm thick formulations of polypeptide used for continuous release of peptides, including growth hormones, covalently conjugated to the polymer. U.S. Pat. No. 5,134,122 to Orsolini issued Jul. 28, 1992 for "Method for Preparing a Pharmaceutical Composition in the Form of Microparticles," appears to teach a process for preparing a ground polymeric product containing salts of peptides including growth hormones comprising compressing, heating and extruding mixed polymeric powder and salts and grinding the resultant product. A sandwich device for release of insulin appears to be described in Yamakawa, I., et al. (1993), "Controlled Release of Insulin from Plasma-Irradiated Sandwitch Device Using Poly-DL-lactic acid," J. Pharm. Soc. Japan 16:182–187. A very small "implant" injectable through a 16-gauge needle appears to be disclosed in Stoeckemann, K. and Sandow, J. (1993), "Effects of the luteinizing-hormone-releasing hormone (LHRH) antagonist ramorelix (hoe013) and the LHRH agonist buserelin on dimethylbenz[a] anthracene-induced mammary carcinoma: studies with slow-release formulations," J. Cancer Res. Clin. Oncol. 119:457–462, which appears to have a longer release time and be more clinically effective than microparticles.

Polymeric implants made of polylactic acid and polyglycolic acid polymers and copolymers also appear to have been described. U.S. Pat. No. 4,801,739 to Bays et al. issued Mar. 17, 1987 for "Biodegradable Prosthetic Device," appears to disclose a ventilation tube for the ear in which the degradation rates of various portions of the implant are varied by adjusting the molecular weight of the polymer e.g. with irradiation.

Polymeric implants used for drug release appear to include those formed from polylactic and polyglycolic acid polymers and copolymers. U.S. Pat. No. 3,976,071 to Sadek issued Aug. 24, 1976 for "Methods of Improving Control of Release Rates and Products Useful in Same," appears to describe the effects of active agents dispersed in the polymer versus solid solutions of the active agent in the polymer. U.S. Pat. No. 4,011,312 to Reuter et al. issued Mar. 8, 1977 for "Prolonged Release Drug Form for the Treatment of Bovine Mastitis," appears to disclose a cylindrical bougie for insertion into the teat canal of a polymer and an antimicrobial agent dispersed therein.

U.S. Pat. No. 4,048,256, 4,095,600 and 4,122,129 to Casey, et al. issued Sep. 13, 1977, Jun. 20, 1978, and Oct. 24, 1978 respectively, for "Normally-Solid Bioabsorbably Hydrolyzable Polymeric Reaction Product," appear to disclose polymerization methods for producing polymers into which active ingredients may be incorporated. Such devices appear to include sandwich devices, intra-uterine devices, and bandages. U.S. Pat. No. 4,076,798 to Casey et al. issued Feb. 28, 1978 for "High Molecular Weight Polyester Resin, The Method of Making the Same, and the Use Thereof as a Pharmaceutical Composition," appears to be a related patent and also appears to disclose intrauterine devices for releasing drugs.

U.S. Pat. No. 4,293,539 to Ludwig et al. issued Oct. 6, 1981 for "Controlled Release Formulations and Method of Treatment," appears to disclose the incorporation of an active ingredient into a polymer by solubilization of the polymer and active agent in a common solvent and extruding into rods of 2 to 7 mm in diameter and 40 to 80 mm in length, followed by implantation of the rod under the skin of an animal. U.S. Pat. No. 4,832,686 to Anderson issued May 23, 1989 for "Method for Administering Interleukin-2," appears to disclose the use of low molecular weight polylactic acid/polyglycolic acid polymers or copolymers for implants of putty-like consistency for intracranial or other implantation. PCT Patent Publication WO 92/11843 published Jul. 23, 1992 by Alza Corporation for "Bioerodible Devices and Compositions for Diffusional Release of Agents," appears to disclose the preparation of sheets and rods (2 mm diameter ×1 cm length) with polymers, active ingredients and "required excipients" in which the release rate is not dependent on erosion of the polymer.

Implants of polylactic or polyglycolic acid polymers or copolymers appears to have been used in bone healing applications. Tencer, A. F., et al. (1989), "The effect of local controlled release of sodium fluoride on the stimulation of bone growth," J. Biomed. Materials Res. 23:471–589, appears to disclose dissolution of sodium fluoride and polylactic acid polymer in acetone followed by driving off solvent and rolling into sheets or rods which were inserted into rabbit femurs. The sodium fluoride appears to have been released in a high initial burst followed by a decrease over a period of several days to a steady state. It appears that best healing was shown in rabbits having the sodium fluoride implants after eight weeks.

Biodegradable polymeric scaffold systems seeded with cells appear to be useful for culture of specific types of cells in vitro. U.S. Pat. No. 4,963,489 to Naughton et al. issued Oct. 16, 1990 for "Three-Dimensional Cell and Tissue Culture System," appear to disclose the use of a polymeric matrix which may be made of polyglycolic acid polymers, for culture of cells such as skin, liver, pancreas, bone marrow, osteoblasts and chondrocytes, etc. in vitro. The seeded matrix may be transplanted in vivo. Related U.S. Pat. No. 5,032,508 to Naughton et al. for "Three-Dimensional Cell and Tissue Culture System," contains a similar disclosure. These patents do not appear to disclose incorporation of growth factor into the polymeric matrix. A further related U.S. Pat. No. No. 5,160,490 to Naughton et al. issued Nov. 3, 1992 for "Three-Dimensional Cell and Tissue Culture Apparatus," appears to disclose that hip prostheses coated with three-dimensional cultures of cartilage may be implanted into patients. This patent also appears to disclose that proteins can be "added to" the matrix or coated on. No methods of "adding" such proteins or release kinetics appear to be described.

Polymeric scaffolds seeded with cells for cellular growth and implantation for cartilage regeneration made from polyglycolic acid/polylactic acid copolymers appear to be disclosed in U.S. Pat. No. 5,041,138 to Vacanti, et al. issued Aug. 20, 1991 for "Neomorphogenesis of Cartilage in Vivo from Cell Culture." This patent appears to teach that growth factors may be incorporated into the polymers but does not appear to provide any methods for doing so. The patent also appears to teach that implantation of the polymeric scaffolding alone without chondrocytes does not result in cartilage formation. Freed, L. E., et al. (1993), "Neocartilage formation in vitro and in vivo using cells cultured on synthetic biodegradable polymers" J. Biomed. Materials Res. 27:11–23, appears to disclose the use of cell-seeded porous polylactic acid and fibrous polyglycolic acid polymers to prepare cartilaginous implants for use in reconstructive or orthopaedic surgery. Apparently no growth factors were added to the polymers. Vacanti, C. A., et al. (1993), "Tissue Engineered Growth of Bone and Cartilage," Transplantation Proc. 25:1019–1021, appears to disclose the use of cell-seeded polyglycolic acid polymeric mesh for implantation on the backs of nude mice to grow bone and cartilage. The use of growth factors in the polymer does not appear to be described. In a review article by Langer, R. and Vacanti, J. P. (1993), "Tissue Engineering," Science 260:921–926, cell seeded scaffolds for in vitro growth of cartilage and bone appear to be described and it is stated that TGF-β is important in bone repair and that effective delivery systems for this agent will be important.

A number of growth factors appear to have been found to be important in the healing of bone and cartilage, including bone morphogenic protein (BMP) platelet-derived growth factor (PDGF), epidermal growth factor (EGF), insulin-like growth factor-1 (IGF-1), basic fibroblast growth factor (bFGF), and transforming growth factor-β (TGF-β) (Hollinger, J. and Chaudhari, A (1992), "Bone Regeneration Materials for the Mandibular and Craniofacial Complex," Cells and Materials 2:143–151). As reported in Edelman, E. R. and Nugent, M. A. (1991), "Controlled Release of Basic Fibroblast Growth Factor," Drug News & Perspectives 4:352–357, basic fibroblast growth factor (bFGF) appears to be a mitogen for many different cells. However, this growth factor appears to lose most of its activity when subjected to organic solvents and heat in making controlled release implants. Edelman, E. R., et al. (1991), "Controlled and modulated release of basic fibroblast growth factor," Biomaterials 12:619–626, appears to state that polypeptide growth factors have in vivo half lives on the order of seconds to minutes, and that bFGF, a mitogen for fibroblasts and a potent angiogenesis factor useful in tissue repair, is best released by binding to heparin-Sepharose beads. U.S. Pat. No. 5,100,668 to Edelman et al. issued Mar. 31, 1992 appears to discuss systems for controlled release of bFGF, and apparently reveals a high initial release.

Hollinger, J. O., et al. (1990), "Osseous wound healing with xenogeneic bone implants with a biodegradable carrier," Surgery 107:50–54, appears to discuss experiments using implants comprising 50:50 polylactic/polyglycolic acid copolymer made by adding bone morphogenic protein (BMP) to polymer solution in acetone followed by vacuum curing for craniotomy repair. The article appears to report that contrary to earlier reports of successful bone regeneration using BMP, the study could not support such data. Bone morphogenetic protein-2 appears to have been found to improve bone healing in implants having a demineralized dog bone powder matrix (Toriumi, D. M. (1991), "Mandibular Reconstruction with a Recombinant Bone-Inducing Factor," Arch. Otolaryngol. Head Neck Surg. 117:1101–1112.) Heckman, J. D., et al. (1991), "The Use of Bone Morphogenetic Protein in the Treatment of Non-Union in a Canine Model," J. Bone and Joint Surg. 73-A:750–764, appears to describe implants mimicking the size and shape of bone defects made of bone morphogenetic protein copolymerized with polylactic acid as useful in bone healing.

Alper, J. (1993), "Will bone morphogenic proteins pay off?" Bio/Technology 11:649–651, appears to disclose that BMP in a bone powder matrix is used for fracture healing and causes cell differentiation. Marden, L. J. et al (1993), "rhBMP-2/ICBM is superior to DBM in repair of rat craniotomies," J. Dent. Res. Abstracts No. 130, appears to disclose that recombinant BMP in an insoluble collagenous bone matrix provides superior bone healing. Kleinschmidt, J. C. et al. (1993), "A Multiphase System Bone Implant for Regenerating the Calvaria," appears to disclose the use of two biodegradable polymeric disks with bone morphogenetic protein between them placed in craniotomy sites of rabbits to aid in healing and prevent prolapse of soft tissue in the defect.

Thyroid-derived chondrocyte stimulating factor (TDCSF) appears to be described in PCT Publication WO 92/14749 by The Board of Trustees of the Leland Stanford Junior University Sep. 3, 1992, as useful for the culture of chondrocytes in vivo and for developing cartilage implants in vitro and for in vivo use in cartilage and bone defect repair. It does not appear that any methods for making implants or release kinetics are taught. PCT Publication WO 93/15767 by Merck & Co, Inc. Aug. 19, 1993 appears to disclose implants made of bioerodible polymers selected from poly (orthoester) or polyacetal and a prostaglandin or β-estradiol implanted at the site of desired bone growth as useful in bone healing.

Transforming Growth Factor β (TGF-β) has been studied for its effects on cell growth. Silberstein, G. B. and Daniel, C. W. (1987), "Reversible Inhibition of Mammary Gland Growth by Transforming Growth Factor—β," Science 237:291–293 appears to report that slow-release polymeric pellets (made of ethylene vinyl acetate copolymer) inhibited mouse mammary growth. U.S. Pat. No. 5,053,050 to Itay issued Oct. 1, 1991 for "Compositions for Repair of Cartilage and Bone," appears to disclose a biodegradable viscoelastic matrix dipped in a solution comprising chondrocytes or osteoblasts which have been cultured in a medium containing TGF-β used for bone and cartilage repair. The growth factor does not appear to be incorporated into the polymer.

Hollinger, J. and Chaudhari, A (1992), "Bone Regeneration Materials for the Mandibular and Craniofacial Complex," Cells and Materials 2:143–151 appears to disclose that TGF-β is released in a latent form at a fracture site, and activated by proteolytic enzymes. In its activated form, TGF-β may be involved in bone remodeling, promote conversion of mesenchymal cells into cartilage cells and enhance production of collagen, fibronectin and plasminogen activating factor in osteoblasts. TGF-β belongs to a family of factors, including two cartilage induction factors previously known as CIF-A and CIF-B, now known as TGF-$\beta_1$ and TGF-$\beta_2$, inhibin, and the BMP's. TGF-β is known for its antiproliferative effects on cells, particularly epithelial cells, but inhibition is also common for mesenchymal cells such as fibroblasts and endothelial cells. In some cases such effects correlate with augmented cellular differentiation. TGF-β has been shown to have both stimulatory and inhibitory effects on proliferation of cultured osteoblasts in different studies. It has been shown to be crucial for wound healing, and is transformed to its active form under acidic conditions such as those produced by bone resorption or macrophages.

Drug release kinetics from a polylactic acid/polyglycolic acid copolymer related to Nafarelin, a peptide hormone, have been reported in Sanders, L. M., et al. (1986), "Prolonged Controlled-Release of Nafarelin, a Luteinizing Hormone-Releasing Hormone Analogue, From Biodegradable Polymeric Implants: Influence of Composition and Molecular Weight of Polymer" J. Pharm. Sciences 75:356–360. The implant appears to have been prepared by melt extrusion of a blend of the compound with the polymer and release has a triphasic profile characterized by a secondary phase of lower release preceded and followed by phases of higher release.

Lewis, D. H. (1990), "Controlled Release of Bioactive Agents from Lactide/Glycolide Polymers," in Biodegradable Polymers as Drug Delivery Systems, Chasin, M. and Langer, R., eds, New York, 1–41, appears to disclose a number of factors affecting drug release kinetics. This reference also appears to report that growth hormones in these systems have at best been able to provide only about two week's duration of biological activity.

U.S. Pat. No. 5,004,602 to Hutchinson issued Apr. 2, 1991 for "Continuous Release Pharmaceutical Compositions Formed by Freeze Drying Acetic Acid Solutions of Polylactide" and related U.S. Pat. No. 4,767,628 to Hutchinson issued Aug. 30, 1988 for "Continuous Release Pharmaceutical Compositions," appear to disclose the use of low molecular weight polymers to cause the two phases of release caused by matrix diffusion and degradation of polymer to overlap.

Hollinger, J. (1993), "Factors for Osseous Repair and Delivery: Part II," reviews factors important in bone healing such as porosity of implants, and states that information relative to optimal pore sizes for osteoconduction is lacking. The article further appears to disclose that by manipulating the biodegradation of the delivery system, the release kinetics of regenerative factors can be tailored for the wound healing chronobiological continuum, and states that chondroosteogenic factor is not needed after the fifth day. Microencapsulating cytokines (bone growth and inductive factors) for pulsed release two to five days after implantation is apparently recommended.

K. Athanasiou et al. (1993), "Use of Biodegradable Implants for Repairing Large Articular Cartilage Defects in the Rabbit," Proc. 38th Ann. Mtg. Orthopaedic Research Soc. Feb. 18, 1992, discloses that 50:50 poly lactide-coglycolide polymeric implants having an average molecular weight of 12–15kD and containing demineralized bone powder used to fill osteochondral cylindrical defects of 4.0 mm diameter and 6mm depth degraded over a period of 8 weeks under conditions of functional joint loading. Successful bone and cartilage repair were observed. Residual polymer was observed to be present at 8 weeks.

U.S. patent application Ser. No. 07/914,992 filed Jul. 16, 1992 discloses a resorbable implant based on independently gelling polymers of a single enantiomeric lactide. Said implant is capable of carrying a bioactive compound; however, said bioactive material is not released in a continuous manner over a period as long as eight weeks.

SUMMARY OF THE INVENTION

A biodegradable, porous, polymeric implant structural material is provided which includes a bioactive agent which is preferably uniformly incorporated therein. In a preferred embodiment, during use in an in vivo environment the implant material provides continuous, smooth release of the bioactive agent over all or some of the degradation period of the polymer. In a preferred embodiment, the bioactive agent is released at all times during which the polymer remains undegraded.

The bioactive agent may be any substance, such as a therapeutic agent or enzyme, whose controlled, continuous release over a prolonged period (e.g., some or all of the degradation period of the polymer) is desired. The bioactive agent is preferably hydrophobic, i.e. does not readily dissolve in water. Preferably the bioactive agent is a protein, such as a degradation enzyme, cytokine or cytokine inhibitor, and more preferably a growth factor. Osteochondral growth factors are preferred. Preferred growth factors include platelet-derived growth factor (PDGF), epidermal growth factor (EGF), insulin-like growth factor-1 (IGF-1), basic fibroblast growth factor (bFGF), thyroid-derived chondrocyte stimulating factor (TDCSF), bone morphogenetic protein (BMP) and transforming growth factor-beta (TGF-$\beta$). TGF-$\beta$ and growth factors having similar properties are more preferred. As will be appreciated by those skilled in the art, combinations of bioactive agents may be used. The bioactive agents may be derived from a variety of sources, synthetic and natural, and include recombinant polypeptides.

The amount of bioactive material in the implant structural material may be adjusted to achieve the desired dosage. Preferably, the implant material contains between about 0.01 ng and about 1 mg of the bioactive agent per milliliter of polymer or polymeric implant material.

The term "continuous" as used herein means that bioactive agent is released constantly without substantial interruption.

The term "uniform composition" referring to the implant material and "uniformly incorporated," referring to the bioactive agent, means that the chemical makeup of the implant material is substantially uniform throughout. In a preferred embodiment, Applicants have shown that the implant material preferably does not contain pockets of encapsulated bioactive agents or other materials. Its microporosity is also preferably substantially uniform.

Figure 4:
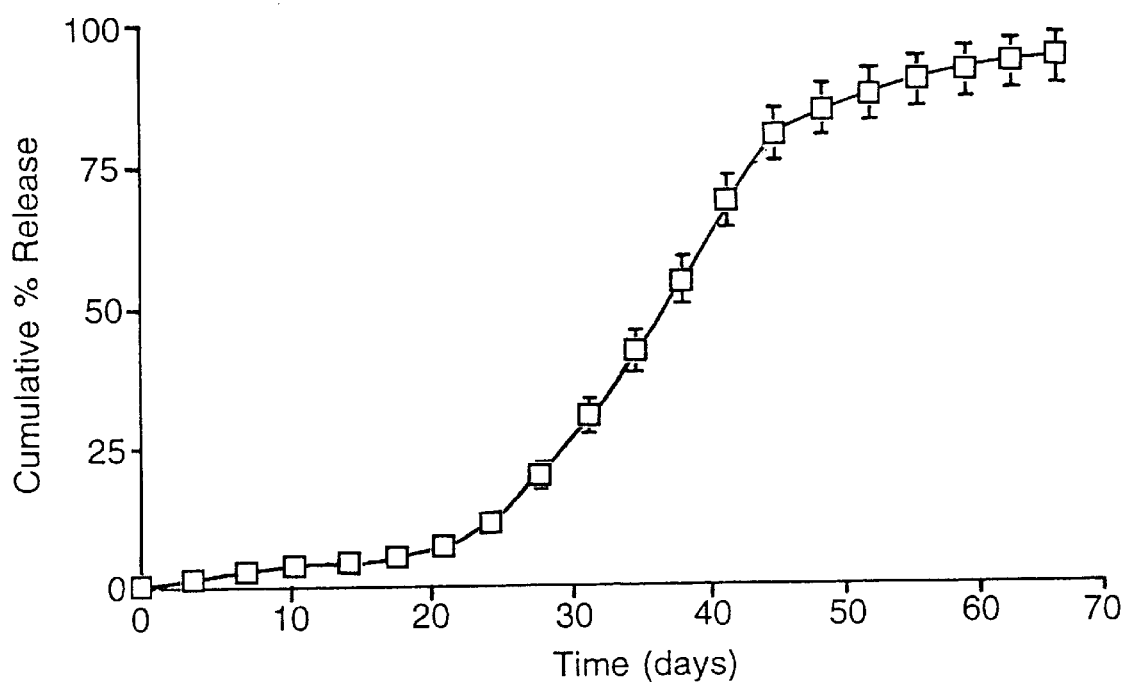
FIG. 4 is a cumulative release profile of polypeptide from an implant over a ten-week period. The release kinetics follow a sigmoidal pattern and more than 95% of the original polypeptide is released.

The term "smooth" as used herein means that the graph of the cumulative amount of bioactive agent released over time rises smoothly without substantial and sudden changes in the slope of the curve (see e.g., FIG. 4, which shows a "smooth" graph of the cumulative amount of bioactive agent released over time).

The implant material preferably has a micropore size between about 50 and about 200 micrometers. More preferably the porosity of the implant matches the porosity of the tissue into which the implant material is intended to be placed. Preferably the porosity of the implant material accounts for more than 50% of the implant material's volume. The implant material may also comprise a plurality of passages (macropores) having a preferred diameter between about 1.0 and about 2.0 mm. The pores and passages are preferably designed to facilitate ingrowth of tissue into the implant in the in vivo environment. The implant material does not necessarily contain cells seeded into the implant or cultured therein in an in vitro environment prior to implantation, as the inventors hereof have discovered such cells are not required for good tissue healing.

Any suitable biodegradable polymeric material may be used, e.g. polyanhydrides and aliphatic polyesters. The implant structure/material is preferably composed of an aliphatic polyester, more preferably comprising polylactic acid (PLA), polyglycolic acid (PGA), and mixtures thereof, and most preferably is composed of a 50:50 mixture of copolymer of PLA and PGA. The polymer preferably has an average molecular weight between about 10,000 daltons and about 100,000 daltons prior to use, preferably between about 40,000 daltons and about 70,000 daltons.

The polymeric implant structure/material may be manufactured so as to have mechanical properties, e.g. stiffness and compressibility, matching those of the surrounding tissue. Implant materials having mechanical properties matching those of bone, cartilage, tendon, skin, ligament, cementum, etc. may be manufactured by the processes of this invention.

The implant structure/material may be used to make various types of implants. Preferably the implants are used for tissue healing, more preferably healing of osteochondral defects. The implant structure/material of this invention may be used in combination with other phases, layers, or supporting structures. Preferred implants of this invention are the two-phase layered biodegradable polymeric implants described in U.S. Ser. No. 08/123,812 filed Sep. 20, 1993, incorporated herein by reference. Most preferred are two-phase implants having one phase with mechanical properties and/or porosity matching those of bone and a second phase with mechanical properties and/or porosity matching those of cartilage. The bioactive agent may be incorporated into both phases or, preferably, only into the bone or cartilage phase.

Another preferred embodiment of this invention is a single-phase implant having the mechanical properties and porosity of cartilage or bone and incorporating a growth factor such as TGF-$\beta$.

The polymeric implant may be any size or shape. A preferable shape is cylindrical. A preferable size is less than or equal to about 1 cm×1 cm for an implant to be inserted at a bone/cartilage juncture.

Figure 1A:
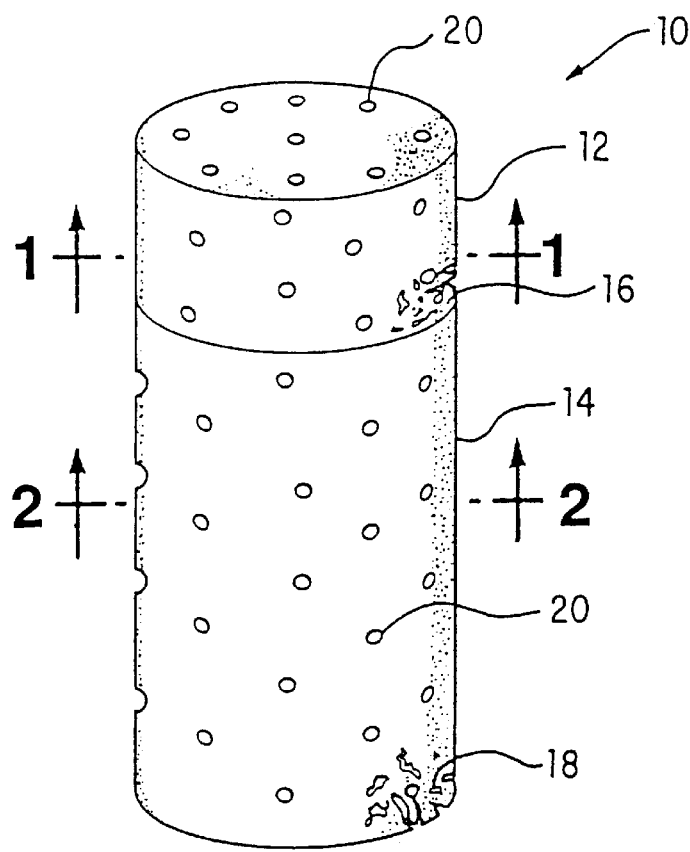
FIG. 1A is a perspective view of a two-phase layered structure/material.

Turning now to the drawings, a carrier/implant 10 is illustrated in FIG. 1A comprising a first bioerodible polymeric structure/material 14 and a second bioerodible polymeric structure/material 12. First structure/material 14 and second structure/material 12 are preferably made from a copolymer-based material of polyglycolic acid (PLG) and polylactic acid (PLA) in a 50/50 concentration of each. Also present in the PLA/PLG copolymer material may be an enzyme homogeneously dispersed within the copolymer which may enhance the degradation of the polymeric substance.

Referring to FIG. 1A, first structure/material 14 is bonded to second structure/material 12, wherein structure/material 14 includes a body having dissimilar mechanical and porosity properties from material 12. Materials 14 and 12 may both include enzymes and therapeutic agents in addition to numerous pores 16 and 18 formed within first structure/material 14 and second structure/material 12, respectively. Pore size varies depending upon the process by which structures/materials 12 and 14 are processed. Preferably, porosity within each structure/material 12 or structure/material 14 is more than 50% of the respective structure/material volumetric area. Moreover, pore size can range between 50 and 200 $\mu$m. However, it is to be appreciated that pore density as well as pore size can vary outside these ranges depending upon the particular manufacturing process chosen, as described herein below. Preferably, structure/material 12 is manufactured having a porosity which generally matches the porosity of the surrounding tissue into which carrier/implant 10 is placed. Similarly, structure/material 14 can be manufactured to a porosity substantially equal to its surrounding tissue. Thus, depending upon the specific application desired, the method of manufacturing carrier/implant 10 can be quickly and easily altered to contain pores of varying size and density.

Carrier/implant 10 can also be perforated with a plurality of passages 20 extending partially or completely through carrier/implant 10. Passages 20 are suitably placed to provide additional sites or locations into or onto which surrounding tissue can enter and/or temporarily bond. Passages 20 are generally larger in diameter than pores 16 or 18 and can be mechanically placed as described below.

Figure 1B:
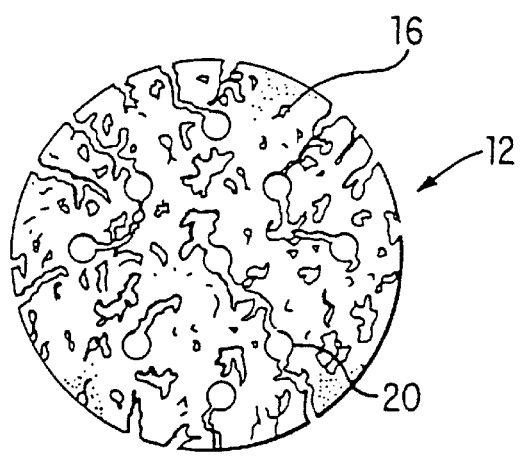
FIG. 1B is a cross-sectional view along plane 1—1 Of FIG. 1A.
Figure 1C:
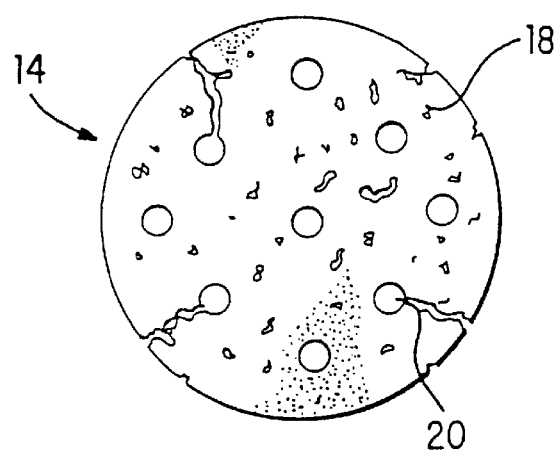
FIG 1C is a cross-sectional view along plane 2—2 of FIG. 1A.

Referring to FIG. 1B, a cross-sectional view of structure/material 12 is shown having numerous access sites or locations formed by pores 16 and passages 20. As shown by the comparisons of FIGS. 1B and 1C, structure/material 14 is less porous than structure/material 12 to substantially match a less porous tissue surrounding structure/material 14 than the tissue surrounding structure/material 12. Moreover, structure/material 12 and 14 can be manufactured having porosity and mechanical properties (such as stiffness and compressibility) to substantially match the porosity and/or mechanical properties of surrounding tissue into which structure/material 12 and 14 is placed.

Figure 2:
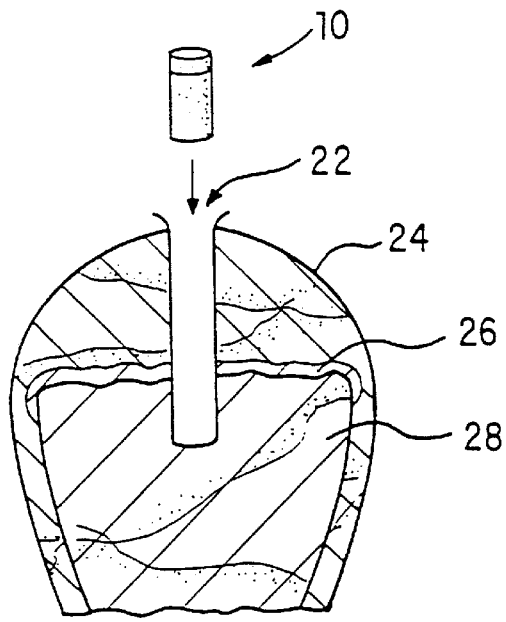
FIG. 2 is a cross-sectional view of an example of a physiological system prepared for implantation of a tissue structure/material.

Tissue carrier/implant 10, having structure/materials 12 and 14 of possibly different porosity and/or mechanical properties, is particularly adapted for placement into a juncture region adjoining tissue areas having dissimilar porosity and/or mechanical properties. Structure/materials within carrier/implant 10 correspondingly can be processed to have porosity and mechanical properties such as stiffness, compressibility etc. to substantially match the properties of the tissue juncture region after implantation. As illustrated in FIG. 2, a physiological environment into which carrier/implant 10 can be placed includes, but is not limited to, a human or animal articular cartilage and underlying bone. Carrier/implant 10 is shown insertable into a bore 22 through skin 24, through underlying cartilage 26 and into bone 28. Alternatively, carrier/implant 10 can be placed entirely within bone 28 to provide structural support to the juncture region between cortical bone and cancellous bone. Accordingly, bore 22 and implantable carrier/implant 10 can be placed into any physiological system having a juncture between dissimilar types of tissue. As used herein, "tissue" includes cellular structure/material found subdermally anywhere within an animal or human anatomy. Any region joining two dissimilar types of tissue (i.e., bone, cartilage, tendon, skin, ligament, cementum, etc.) can be implanted with the bonded dissimilar structure/materials 12 and 14 of carrier/implant 10. By bonding each structure/material together and implanting the combination within a tissue juncture, carrier/implant 10 ensures the tissue juncture remains together during the repair process, which may help to promote rapid healing.

Figure 3:
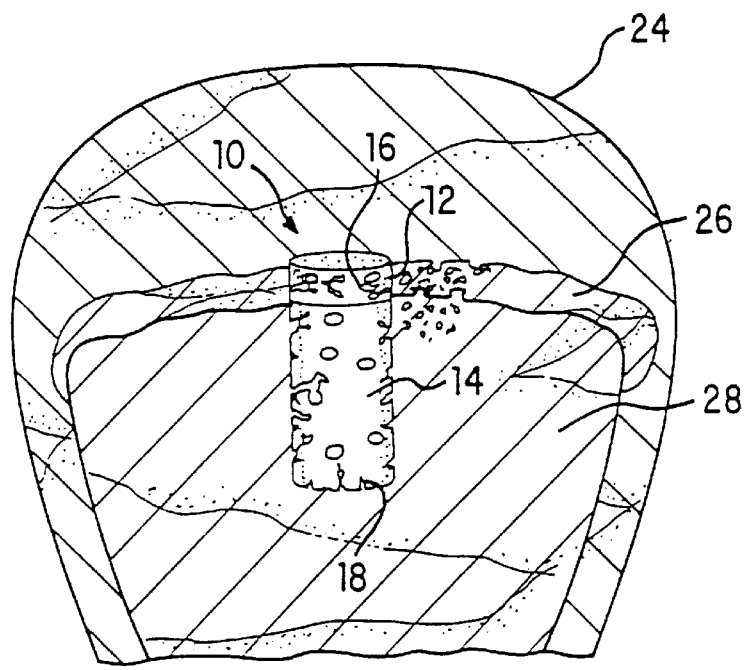
FIG. 3 is a cross-sectional view of an example of a physiological system implanted with a tissue structure/material.

FIG. 3 illustrates carrier/implant 10 fully implanted within dissimilar tissue regions, e.g., cartilage 26 and bone 28. After inserting carrier/implant 10 through hole 22, outer skin 24 is sutured over the bore passage to prevent infection from entering the underlying region. As can be appreciated from the present invention, carrier/implant 10 is produced in any desired shape with differing porosity and/or mechanical characteristics depending upon the size and composition of the target area. In this example, carrier/implant 10 is cylindrical in shape having an outer diameter generally matching the inner diameter of a bore or hole 22 created in the region of interest. However, other shapes can be produced and inserted into the hole. Regardless of the shape used, the carrier/implant can expand to match the internal cavity or bore size prior to or during the bioerodible process. Still further, the proportionate sizes of structure/material 12 and 14 can be varied depending upon the relative location of carrier/implant 10 in relation to the interface region. For example, cartilage 26 may be thicker than that indicated in FIG. 3 such that its thickness would be equal to or greater than the bore 22 depth into bone 28. Consequently, structure/material 14 can be made larger or thicker than structure/material 12 to correspond with the relative shift in boundary between cartilage 26 and bone 28.

Bone 28 generally presents a less porous and stiffer structure/material than overlying cartilage 26. Therefore, as shown in FIG. 3, pores 18 can be made relatively smaller than pores 16. Accorded access sites or locations into pores 18 and 16 are dissimilar to generally match surrounding bone 28 and tissue 26, respectively. During the time in which bone 28 and cartilage 26 tissue regenerate and grow into the damaged region partially replaced with carrier/implant 10 and pores 18 and 16, respectively, carrier/implant 10 maintains a somewhat rigid support structure. As the structure of carrier/implant 10 gradually erodes or dissolves, regeneration of tissue takes place which replaces the structural support lost during erosion. Accordingly, the present invention serves to provide better anchorage of regenerated tissue in the damaged or defective region and also provides a temporary support structure which need not be subsequently removed as in conventional rods and pins. The bioerodible carrier/implant 10 is particularly useful in juncture regions where slow healing occurs due to lack of vasculature or cell population.

As shown in FIGS. 2 and 3, carrier/implant 10 is insertable as a press-fit in the osteochondral defect region. The swelling characteristics of the bioerodible structure/material 14 and 12 is expected to improve retention of carrier/implant 10 within the defect region. Comparable porosity and/or mechanical properties of structure/materials 14 and 12 to that of surrounding tissue avoids stress concentrations during joint articulation. By matching characteristics such as porosity, exchange of nutrients from the tissue into carrier/implant 10 is provided as though normal growth patterns occur. Confocal laser scanning micrographs of carrier/implant 10 may illustrate carrier/implant 10 having pores 16 and 18 of varying sizes. The carrier/implant 10 is generally microporous and its pores are preferably interconnected throughout the cross-sectional area of the structure/material.

The polymeric implant material of this invention may comprise other additives such as surfactants, solubilization enhancers and the like. For example, Serum Albumin (SA), such as Bovine Serum Albumin (BSA) or Human Serum Albumin (HSA) may be present. It is preferred that if serum albumin is present, it be kept to a minimum. Some commercial preparations of desired bioactive agents contain HSA, e.g., TGF-β of R&D Systems, Minneapolis, Minn. 55413, which contains 50 μg HSA/μg recombinant human TGF-β$_1$. It is preferred that the amount of serum albumin be kept to less than about 100 μg SA/μg bioactive agent. It has been discovered by the inventors herein that larger amounts of serum albumin may prevent uptake of polypeptides by the polymer during implant manufacture and may alter in vivo release kinetics (such as causing an initial large burst of polypeptide to be released after implantation). When serum albumin is kept to a minimum, the polypeptide may be incorporated into and onto the polymer so that it is continuously and smoothly released over some or all of the degradation period of the implant.

The implant material of this invention is capable of releasing the bioactive agent over its entire period of degradation. Preferably, this release period is at least about six weeks up to about twelve weeks and more preferably, at least about eight weeks up to about ten weeks. In use, it has been found that superior cartilage healing occurs when the growth factor is released over such a period of time.

The invention also relates to a method of making a biodegradable, porous, polymeric implant material having a biologically active agent incorporated therein, which during use in an in vivo environment preferably provides substantially continuous release of the bioactive agent over some or all of the degradation period of the polymer, comprising:

a. solubilization of said polymer in a suitable organic solvent to form a first solution. Any organic material capable of solubilizing the polymer may be used so long as evaporation of the solvent does not leave residues which cannot be removed and which would deleteriously alter the bioactive agent or polymer. Acetone and methylene chloride are preferred solvents with acetone being most preferred.

b. addition of a second solution or suspension, preferably an aqueous solution or suspension, of said bioactive agent to said first solution to form a third solution. Solubility enhancers such as surfactants as known to the art may be included as required. Bis phosphate which retards or inhibits osteoclasts, may be included, for example in patients suffering from osteoporosis, where bone formation is difficult to achieve, in part because osteoclasts are overactive. Otherwise bis phosphate would not be a desirable additive. It is preferred that less than about 100 μg serum albumin per μg bioactive agent be used.

c. removal of solvent from said third solution to form a solid mass. It is preferred to precipitate the polymer and associated bioactive agent from solution with a precipitating agent known to the art such as ethyl alcohol to form a solid gummy mass comprising polymer and bioactive agent. The third solution may also be subjected to drying such as with heat and/or vacuum. A precipitation step is preferred as this removes undesirable solvent residuals.

d. treatment of said solid mass in a mold with relatively high vacuum, such as between about 8 and about 20 microbars, preferably about 10 microbars.

The above steps are preferably performed at a temperature below the degradation temperature of the bioactive agent, e.g. preferably not more than about 42° C. when TGF-β is the bioactive agent. It is preferred that the completed implants be stored at low temperatures, e.g., about −50° C., prior to use so as to inhibit degradation of bioactive agents such as TGF-β which tend to degrade when stored at room temperature.

Preferably, the solid mass is subjected to vacuum in a lyophilizer at room temperature for at least about twenty hours. In a preferred embodiment, prior to this step, the polymer is subjected to vacuum via vacuum pump, e.g., about 20 millibars in a desiccator and rolled flat in several stages. The vacuum treatments help cause the polymer to achieve the desired porosity. Preferably, a uniform porosity with an average pore size between about 50 and about 200 micrometers with pores accounting for more than about 50% of the implant volume is achieved. As will be appreciated by those skilled in the art, the viscosity of the polymer and the magnitude and duration of vacuum, as well as temperature conditions, can be varied to vary the porosity.

Uniform incorporation of the bioactive agent into the polymeric implant material may be achieved by solubilizing the polymer and mixing therewith a uniform solution or suspension of the bioactive agent such that the agent is substantially evenly distributed in the solution. Thereafter, the solvent may be removed, preferably by precipitation followed by treatment with low vacuum, and the polymer may be pressed into a mold and subjected to relatively high vacuum, e.g. about 8–20 μbars, until an implant material having the desired porosity and/or mechanical properties is achieved.

The method may also be varied in order to produce an implant material having mechanical properties and porosity matching those of the target tissues as described above. When the implant material is to have the properties of bone, it is preferably subjected to oven curing, preferably at a temperature of between about 40 and about 47° C. for a period of up to about 48 hours. As the implant material includes bioactive agents the temperature is preferably kept below temperatures which would cause substantial degradation of the bioactive agent.

The preferred method also involves piercing the polymer inside the mold with pins or other sharp implements prior to vacuum treatment in the lyophilizer so as to form passages through the implant having an average diameter of about 1.0 to about 2.0 mm. In another preferred method, the pins or other sharp implements are placed inside the mold and left there during the curing process to form the passages. Preferably such passages are placed substantially parallel and perpendicular to the long axis of the implant and are spaced apart from each other a distance of about 1 to about 2 mm.

A method for using the implant material of this invention is also provided. The method allows continuous in vivo delivery to a patient of a regulated amount of a bioactive agent for a desired time period and includes implanting into tissue of said patient a porous implant material including a biodegradable polymer with a bioactive agent incorporated therein, said bioactive agent being present in an amount sufficient to provide a therapeutically effective dosage, and said implant material being present in an amount sufficient to degrade over the desired time period. A "regulated amount" of bioactive agent is an amount with a defined and predictable dosage at any given time. As shown herein, the implant materials of this invention are capable of delivering bioactive agents in slowly increasing amounts, rising to a predictable maximum peak, and slowly descending to a minimum amount. This predictability of release allows for the design of implants for delivering effective, non-toxic amounts of bioactive agents over a desired time period. This predictability of release also allows for the design of implants for delivering substantially low amounts of bioactive agents during the first weeks of use.

Preferably an implant composed of the biodegradable implant material of this invention is used for healing osteochondral defects and the bioactive agent is a growth factor, such as TGF-$\beta_1$. The implant material of this invention is preferably present in an amount sufficient to provide a release period of eight weeks.

Description of the Preferred Embodiments

In a preferred embodiment, the implant materials of this invention are especially well-suited to promote healing of osteochondral tissue, and in particular articular cartilage defects. As shown herein, superior cartilage healing may be achieved using an implant made with the materials of this invention capable of controlled, smooth release of TGF-$\beta$ over a period of at least about eight weeks.

The implant material of a preferred embodiment has an average pore size between about 50 and about 200 $\mu$m and its porosity accounts for more than 50% of its total volume. In addition, it has passages or macropores having a diameter of between about 1.0 and about 2.0 mm. The implant thus forms a scaffolding which promotes the flow of body fluids and allows ingrowth of cartilage cells during the healing process. Without wishing to be bound by any theory, applicants suggest that when TGF-$\beta$ is uniformly incorporated in the polymer by the method disclosed herein, it has a chemotactic effect in promoting cell ingrowth and, in the in vivo environment surrounding the newly ingrowing cells, becomes released, in turn stimulating differentiation of the cartilage cells. Meanwhile, the polymer biodegrades by hydrolysis and the healing tissue fills the space.

It is preferable that the growth factor be continuously available over the entire healing period. Moreover, it is preferred that a reduced amount of growth factor be initially released. Furthermore, such a reduced amount of growth factor is preferably released while the implant is degrading at a substantially higher rate (on a percentage basis) than the growth factor is being released. If a relatively large amount of growth factor were to released within the first few days of the healing process it is possible that such an initial burst might prevent migration of relatively undifferentiated mesenchymal cells throughout the defect by causing too early cell differentiation of chondrocytes. In tissues such as cartilage, where a surplus of mesenchymal cells is typically not available to migrate into the defect, it is preferable to ensure that those which are available are able to do so. Comparative data shows improved migration of cells into the implant material when TGF-$\beta$ is present.

By the methods of this invention, the bioactive material is intimately associated with the polymer. Tests of polymer fragments broken off during the degradation process have shown that they have growth factor attached. Thus, a continuous smooth release of growth factor may be provided over the entire degradation period of the polymer.

The implant materials of this invention preferably mimic the mechanical properties and porosity of the tissues in which they are placed. The methods of this invention allow the stiffness and compressibility as well as the porosity of the material to be varied as desired. Methods of testing such properties are well-known to the art, for example via measurements of creep deformation and stress relaxation as described in co-pending U.S. patent application 07/837,401 incorporated herein by reference. Numerical values for various mechanical properties of tissues are also known to the art, for example, with respect to articular cartilage, compressive stiffness is in the range of 0.79 MPa±0.36 (Armstrong, C. G., et al. (1982), "Variations in the Intrinsic Mechanical Properties of Human Articular Cartilage with Age, Degeneration, and Water Content," J. Bone and Joint Surgery 64A:88–94), and tensile stiffness is in the range of 1–15 Mpa, and less than 30 Mpa (Akizuki, et al. (1986), "Tensile Properties of Human Knee Joint Cartilage: I. Influence of Ionic Conditions, Weight Bearing, and Fibrillation on the Tensile Modulus," J. Orthopaedic Res. 4:379–392. Cortical bone has a compressive stiffness of about 7,000 MPa (Fung, Y. C. (1981), "Biomechanics—Mechanical Properties of Living Tissues," Springer Verlag, New York pp. 384–385), and a tensile stiffness of about 17,000 MPa (Reilly et al. (1974), J. Biomech. 7:271–275; Reilly and Buskin (1974), J. Bone and Joint Surgery 56A:1001–1022. Ligaments and tendons lack compressive stiffness. Ligaments have a tensile stiffness of about 600 MPa (Woo, S. et al. (1987), "The Biomechanical and Morphological Changes in the Medial Collateral Ligament of the Rabbit after Immobilization and Remobilization," J. Bone and Joint Surgery 69A:1200–1211); and tendons have a tensile stiffness of about 800 MPa (Woo, S. (1982), "Mechanical Properties of Tendons and Ligaments," Biorheology 19:385–396). Further, such tissues are readily available to the skilled worker to use for comparison with the polymeric materials of this invention, in order to provide matching of the mechanical properties of the implant material to those of the tissue in which it is to be placed.

In preparing the polymeric implants of this invention, the viscosity of the polymer may be varied, as well as the amount of vacuum applied, compression applied prior to curing, and during curing, as well as curing temperature and temperatures during application of vacuum, and time periods for various process steps. These conditions may be varied in accordance with the properties desired in the implant material.

To increase porosity the process preferably utilizes higher vacuums while the polymer is wet. Rolling of the polymer at this stage tends to increase surface area leading to faster evaporation, breaking bubbles of trapped solvents and tending to cause formation of numerous pores. The polymeric material is naturally elastic to visco-elastic, and may be made stiffer by longer curing at higher temperatures, and by higher vacuum to reduce moisture content.

In addition to, or instead of growth factors such as TGF-$\beta$, the implant materials of this invention may also include enzymes, cytokines, hormones, and medicinal substances for which a controlled, predictable release pattern is desired. The invention has been illustrated using trypsin inhibitor as well as TGF-$\beta$.

As disclosed herein, the methods of making this invention include the use of polymeric materials of selected molecular weights. As is well-known to the art, a way to adjust the degradation period of biodegradable polymers is by control of molecular weight. The degradation period is further a function of the mechanical properties and physical conformation of the implant material. Applicants have found that their polymers do not show the type of bulk degradation found by prior workers to result in "dose dumping." Instead, the implants of this invention deliver a smooth, predictable, amount of bioactive material over a predictable period of time, and may thus be used in therapeutic methods where accurate prediction of drug release is required so that dosage can be regulated within effective, non-toxic levels.

The foregoing description of the present invention has been directed to particular embodiments. It will be apparent, however, to those skilled in the art, that modifications and changes in both the implant material and the method of making and using the material can be made without departing from the scope and spirit of the invention. It is the intention in the following claims to cover all such equivalent modifications and variations which fall within the true spirit and scope of this invention.

EXAMPLES

Example 1

Continuous Controlled Release

A two-phase implant comprising a bone phase and a cartilage phase is prepared substantially according to the method of U.S. patent application Ser. No. 08/123,812. The bioactive agent, trypsin inhibitor (TI) is added only to the cartilage phase. In each phase, 50:50 poly(DL lactide co-glycolide) (PLG) copolymer with a small inherent viscosity and weight average molecular weight of 53kD is solubilized in 6 ml acetone per 1 g of polymer and precipitated with 10 ml of ethanol per 1 g of polymers to form a solid, gummy mass. Three mg of trypsin inhibitor (TI) is added per implant. The bone phase contains 0.0675 g of polymer. The cartilage phase, which has the TI, contains 0.043 g of polymer. The polymer is packed into a teflon mold and subjected to 10 m Torr vacuum at 4° C. for 24 hours, partially removed, and placed in a lyophilizer under the same conditions for another 24 hours. At the end of the curing period, the implants are completely removed from the mold and stored in the lyophilizer until tested. The implants have a size of 4 mm diameter×6 mm deep.

A total of 84 implants are constructed and divided into seven groups of six control implants and seven groups of six implants with TI. Degradation and enzyme release are examined at t=0, 1, 2, 4, 6, 8 and 10 weeks. Implants are placed in plastic vials containing 5 ml of phosphate buffered saline (PBS), pH 7.4, at 37° C. Every 3.5 days, 1.5 ml aliquots of the PBS are aspirated and immediately frozen. At the end of the test period, implants are removed from the PBS solution, placed in a desiccator at 25 m Torr, and then placed in a freezer at −20° C. until testing. The collected aliquot is thawed for one hour at room temperature prior to testing. TI release characteristics are quantified using the micro bichinonic acid (BCA) assay for protein content. Implant degradation is monitored by measuring molecular weight using gel permeation chromatography, examining compressive properties (using an automated mechanical tester which measures stress relaxation and creep deformation), and performing scanning electron microscopy and gross morphology evaluations to quantitatively observe implant temporal changes.

TI is slowly released at a rate of approximately 1% every 3.5 days for the first three weeks, followed by larger protein release, and a peak of 14% is attained at six weeks. After seven weeks, release subsides to about 2% every 3.5 days. Cumulatively, about 95% of the original TI is released over the 10 week period. Enhanced release is between 3 and 7 weeks. FIG. 4 displays the cumulative percent release of TI from the carrier over the ten-week period. The release kinetics follow a sigmoidal pattern.

Figure 5:
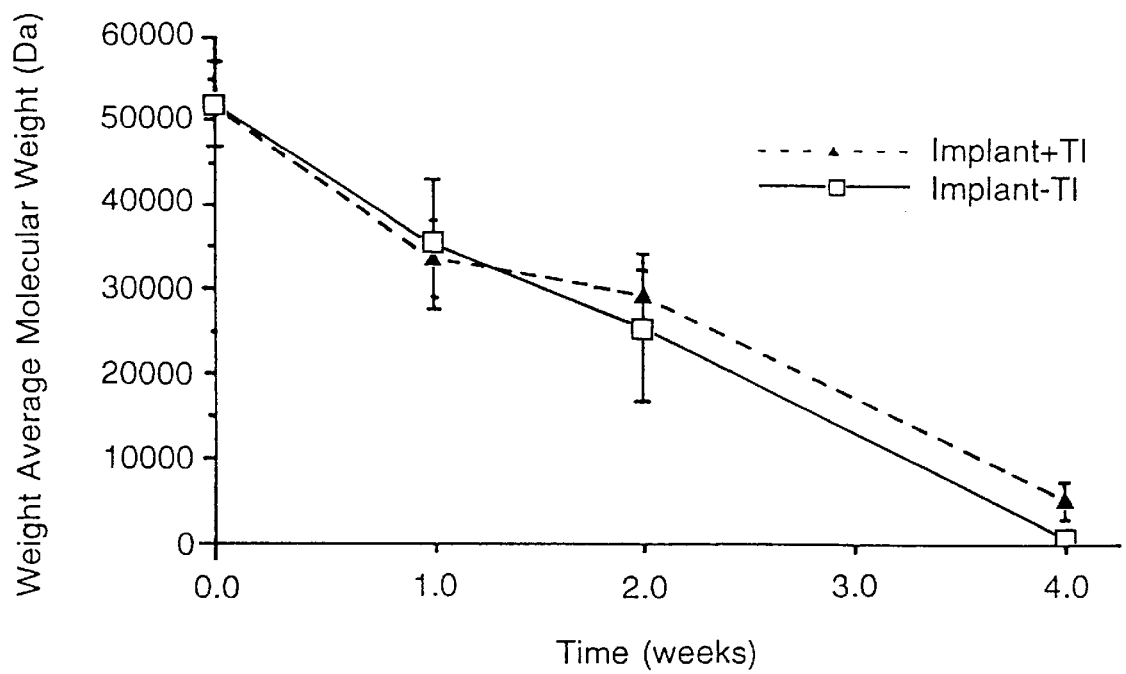
FIG. 5 shows changes in average molecular weight over 10 weeks. A 34% reduction in molecular weight is seen in both experimental and control implants in the first week. The molecular weight then decreases gradually until it has decreased to 1 kD by four weeks.

FIG. 5 displays the temporal change in average molecular weight. The initial molecular weight of the carrier implant and control are 52.5 Kilo Dalton ("kD") and 60 kD respectively. A 34% reduction in molecular weight is seen in both groups during the first week, followed by a continued steady decrease until the molecular weight has decreased to less than 1 kD by the fourth week. There are no significant differences between the two groups at any time period.

Figure 6:
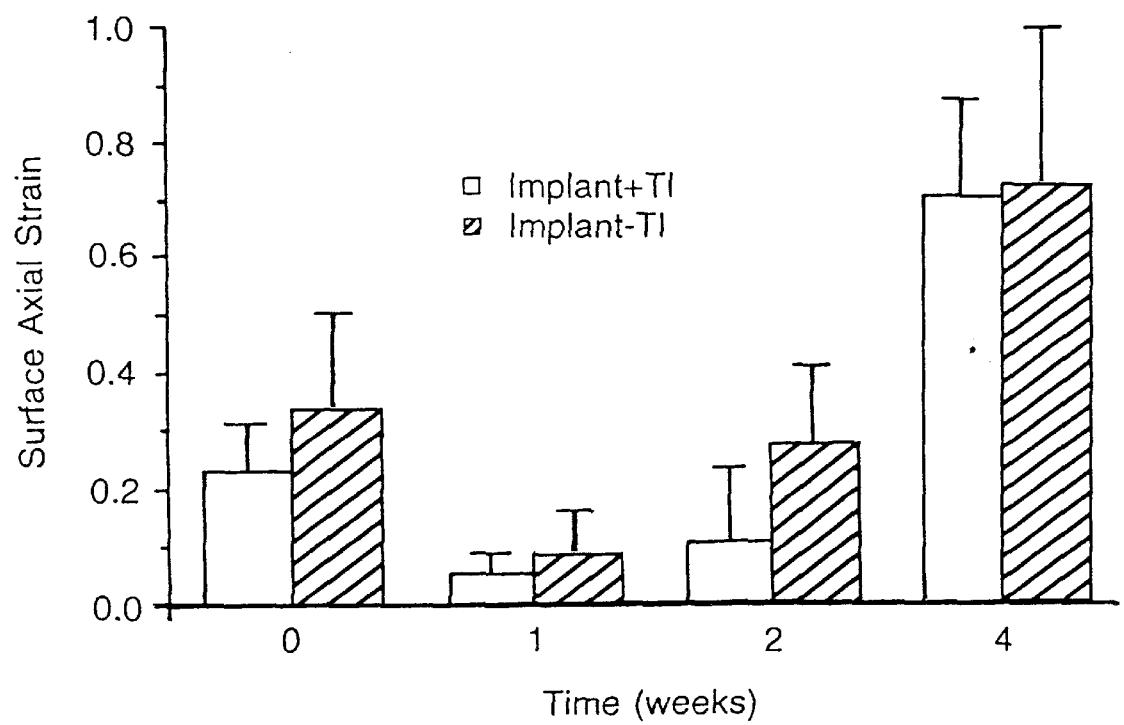
FIG. 6 displays changes in surface axial strain measured one hour after application of a 0.87 N step load under conditions of creep indentation.

FIG. 6 displays the temporal changes in surface axial strain, always measured at one hour after application of a 0.87N step load under conditions of creep indentation. There is a significant decrease during the first week of testing in both groups, followed by an increase during weeks 2–4. The implants change from being smooth and translucent at t=0 week to chalkish white at t=1 week, soft and sticky at t=4 weeks, and dissolved completely by ten weeks. Scanning electron microscopy pictures indicate that TI incorporation increases both the number and size of pores in implants at all time groups.

The TI is released in a progressive, time-dependent fashion instead of in a rapid, burst release. Approximately 95% of the TI originally placed in the implant is released in a gradual fashion over the ten-week test period. This indicates that the TI is intimately associated with the polymer, probably due to its hydrophobic nature, and diffuses into the PBS together with the polymer fragments. Changes in polymer chain length and material weight parallel the release kinetics of TI. The lack of significant TI release (the release was less than 10%) during the first three weeks appears to be advantageous. It also suggests that breakdown of implant structure above a threshold level may be necessary to achieve higher levels of release. Furthermore, TI does not alter the degradation kinetics of the polymer, although there are distinct morphologic differences, supporting the hypothesis that polymer breakdown is the underlying mechanism of TI release.

The decrease in surface axial strain seen at one week indicates an increase in stiffness of the implants, probably due to an initial increase in crystallinity caused by hydrolytic scission of the amorphous regions. It is possible that the PLG material used in the present study has a very low degree of crystallinity, which increases upon degradation and manifests itself in a change in mechanical properties of the implant. The subsequent, twofold increase in surface axial strain indicates decreased stiffness of the implants, likely resulting from the ongoing, continuous breakdown of implant integrity due to polymer degradation.

Without wishing to be bound by any theory of how the invention works, and recognizing that there are many possible explanations, the inventors suggest that the original homogenous implant placed in buffered saline or in the in vivo environment immediately begins to undergo hydrolytic scission of ester bonds. The implants originally maintain their structural integrity despite the drop in their molecular weight in the first four weeks. The initial degradation process is probably more pronounced at the surface of the implant compared to the core because the degradation products formed at the surface are able to freely diffuse into the PBS. This surface diffusion could contribute to the small release of TI seen in the first three weeks. It is likely that the breakdown products and TI released at the center could result in an increase in osmolarity which may have resulted in swelling. In the 4–7 week period the surface of the implant no longer has the ability to halt TI exudation from the center, thus causing rapid TI release. This is supported by the increase in porosity seen with scanning electron microscopy with time.

Example 2

Cartilage Healing

Two-phase biodegradable implants are designed and constructed using 50:50 poly(DL-lactide-co-glycolide) (PLG)

with inherent viscosity of 0.71 dl/gm (weight average molecular weight 65 kD). The implant consists of a "bone" phase that abuts against the underlying bone for anchoring and a "cartilage" phase which interfaces with the adjacent layer of articular cartilage. The polymer is solubilized in acetone and precipitated with ethanol. The gummy "bone" composite is placed under 10 m Torr vacuum for six hours and then packed into a Teflon mold under 10 m Torr and 24° C. for 24 hours. The implants are then partially removed and allowed to remain under the same conditions for 24 hours. New polymer is then solubilized in acetone and combined with the appropriate amount of Transforming Growth Factor-$\beta$ (TGF-$\beta$). The growth factor, recombinant human TGF-$\beta_1$, is solubilized in sterile water, stirred overnight and added to the soft polymer. 2 $\mu$g TGF-$\beta_1$ is dissolved in 0.2 ml sterile water. The TGF-$\beta_1$ preparation provided by R&D Systems contains 100 $\mu$g HSA. The sterile water contains 0.1 mg/ml BSA for implants to be used with rabbits and 0.1 mg/ml of goat serum albumin (GSA) for implants to be used with goats. The appropriate volume of solution to give a total of 50 ng of TGF-$\beta$ is used in the "cartilage" phase only of each implant. The two-phase implants are placed in the mold under 10 mTorr and 4° C. for 24 hours, partially removed, and placed in a lyophilizer under the same conditions for another 24 hours. At the end of the curing period, the implants are completely removed from the mold and stored in the lyophilizer until required for implantation into the host. The curing techniques used for the two phases render the implant porous and the "cartilage" phase softer than the "bone" phase. The two phases are mechanically tested using an automated indenter and modeled using the linear biphasic theory (Mow, V. C. et al. (1980), J. Biomech. Eng. 102:73–84).

Cylindrical, 4mm×6mm, full-thickness defects are created with a low-speed drill, under saline irrigation, in the central posterior medial condyle of each right knee joint, through a posteromedial approach. Defects are filled with carriers containing 50 ng of TGF-$\beta$, implants without growth factor, or are left empty as controls. The animals are allowed free cage activity for either four or eight weeks, prior to sacrifice. A total of 72 New Zealand male white rabbits are used. The quality of healing is examined at four weeks (36 rabbits) and at eight weeks (36 rabbits) using gross morphology, biomechanics, and histomorphometry. Statistically the results are compared with analysis of variance and multiple comparisons tests.

The repair osteochondral defect and adjacent site are biomechanically tested using an automated indenter, under conditions of biphasic creep indentation. The three intrinsic material properties of repair and adjacent cartilage are obtained using a numerical algorithm (Athanasiou et al. (1992), Trans. Orth. Res. Soc. 17(1):172) based on biphasic finite element methods (Spilker et al. (1990), Journal of Biomechanical Engineering, 112:138) and nonlinear optimization techniques. The adjacent site is tested 3 mm anterior to the defect. After biomechanical testing, each osteochondral specimen is sectioned, stained with Alcian blue, and digitized to obtain the geometric parameters needed in the finite element modeling. The Cray supercomputer is used for these analyses. Histologically, each osteochondral specimen is decalcified and stained with hematoxylin and eosin. Sections are analyzed with an image analysis system to measure the percent of trabecular bony repair in each defect.

At four weeks, mild synovitis is observed in the majority of the group having the implant without TGF-$\beta$, in the group having the implant with TGF-$\beta$ or the control group. There is no synovitis noted at eight weeks in any group. Histologically, new bone formation is noted in all control and experimental defect sites. However, control specimens show only partial bony healing with more fibrous tissue present than in either experimental group. This fibrous tissue is noted to reach the articular surface emphasizing the limited healing of control osteochondral defects at eight weeks.

Fifty percent of the animals implanted with TGF-$\beta$ demonstrate the best osteochondral healing with greatest defect bone density and osteoblastic activity. Animals with the implant without TGF-$\beta$ show gross destructive change without an obvious histologic etiology; furthermore all implant is resorbed and no foreign body giant cell reaction is present. Thus, histologically, a clear difference between implants with and without TGF-$\beta$ is observed.

The material properties and thickness of repair and adjacent cartilage of only the eight-week group are shown in Table 1. Corresponding to the histologic findings, the repair cartilage associated with TGF-$\beta$ appears to exhibit greater stiffness (aggregate modulus), and lower permeability, than control or implant alone.

TABLE 1

Material properties and thickness of healing articular cartilage (mean ± SD)

| HEALING | Compressive Modulus $H_A$ (MPa) | $v_s$ Apparent Compressibility | Permeability k × $10^{15}$ (m$^4$/Ns) | Cartilage Height h (mm) |
|---|---|---|---|---|
| Control (n = 4) Empty Defect | .38 ± .13 | .19 ± .18 | 2.55 ± 0.98 | .39 ± .31 |
| Implant (n = 4) No TGF$\beta$ | .35 ± .12 | .29 ± .10 | 2.32 ± 0.47 | .49 ± .23 |
| Carrier (n = 4) 50 ng TGF$\beta$ | .51 ± .22 | .14 ± .08 | 2.15 ± 0.69 | .55 ± .22 |

Example 3

Release of TGF-$\beta$

Release kinetics of TGF-$\beta$-containing polymeric implants are studied using two-phase implants made in accordance with the procedure of Example 2 using BSA rather than GSA. Each implant contains 180 ng of TGF-$\beta$ from R & D Systems, containing 50 $\mu$g HSA per $\mu$g TGF-$\beta$. The amount of TGF-$\beta$ lost during the implant manufacture is determined by bioassay of the solvents used (stimulation of alkaline phosphatase in ROS 17/2.8 cells). When the TGF-$\beta$ is dissolved in water alone, 12.6% is lost in the wash; when 0.1 mg/ml BSA is added, 46.5% is lost; and when TGF-$\beta$ is dissolved in 1 mg/ml BSA+4mM HCl, 71.5% is lost.

Implants ±TGF-$\beta$ (BSA/HCl) are incubated in 1 ml PBS for twelve weeks; every 3.5 days the PBS is removed and stored at −70° C., and fresh PBS applied. TGF-β release is assayed by radioimmunoassay (anti-TGF-$β_1$). Of the 12.64 ng TGF-β released, 7.4% is released during the first three weeks, 22.5% in the second quarter, 27.3% in the third quarter, and 42.8% in the last three weeks.

Fourth passage resting zone chondrocytes are cultured on implants ±TGF-β in Dulbecco's modified Eagle's medium containing 10% fetal bovine serum, 50 μg/ml ascorbate, and antibiotics. At confluence, fresh media are added and after 24 hours, [$^3$H]-thymidine and [$^3$H]-uridine incorporation and alkaline phosphatase specific activity are measured. All parameters are inhibited in cells cultured on the implants with respect to controls. These results indicate that there is a time-dependent, continuous release of TGF-β from the implants supporting previous observations using soybean trypsin inhibitor as a model protein.

Example 4

Preparation of Implant

A biodegradable, porous, two-phase osteochondral implant is made of 50:50 poly(DL) lactide-co-glycolide (PLG) and used as a controlled release delivery system for recombinant human transforming growth factor $β_1$ (rhTGF-$β_1$). The two-phase implant consists of a stiffer bone phase which interfaces with subchondral bone to provide fixation, and a softer cartilage phase which interfaces with a chondral defect. Other design considerations include high porosity at both macroscopic and microscopic levels and use as a scaffold for tissue ingrowth. 4mm×6mm cylindrical two-phase polymeric implants are designed and produced in a mold for implantation in rabbits. 7mm×7mm cylindrical two-phase polymeric implants are designed and produced in a different mold for implantation in goats. The molds are cylindrical in shape and pierced with holes to allow insertion of steel needles during the molding process. Implants are made under sterile conditions; all equipment has been autoclaved and cleaned with a 70% ethanol-distilled water mixture. Containers are kept covered and sealed until used.

The bone phase for the goat implants is made by means of the following protocol: The PGA/PLA is stored at −20° C. After removing from the freezer, it is opened under controlled conditions using nitrogen inside a closed plexiglas chamber so as not to expose it to atmospheric conditions. The polymer is weighed in a 40 mL Teflon beaker. After weighing the beaker and zeroing the balance, the desired quantity of PLG is scooped into the beaker and weighed. For cylindrical implants 7mm in diameter ×7mm in length, 0.9 g PLG is required. The polymer is solubilized in acetone at a ratio of 6mL/mg polymer. Acetone is poured into the beaker and stirred until all polymer is dissolved (substance is a yellowish liquid). Typically about 20 minutes of stirring is required. Upon completion of solution, ethyl alcohol is added to the solution at a ratio of 5 mL/mg polymer. The mixture is stirred for approximately five minutes to form a gum-like polymer in liquid ethanol. The excess ethanol is poured off. Additional ethyl alcohol is added at a ratio of 50 mL/mg polymer, and the mixture is left uncovered for 3–5 minutes at room temperature. The solid is then separated from the liquid. The solid is placed in a Nalgene (PGC Scientifics, Gaithersburg, Md.) desiccator and flattened and sponged to allow escape of excess ethanol. The vacuum pump is operated via a programmable timer. After three minutes, the vacuum is turned off and the polymer rolled with a Teflon bar three times to form a sheet approximately 0.5 mm thick. The sheet is again vacuumed for two minutes and rolling is repeated. After vacuuming for three additional minutes (eight minutes total), the machine is turned off and the polymer weighed.

The total mass is divided into twelve equal portions, weighing each portion, and each portion is placed into a mold, poking with a stainless steel poker. The mold is placed under vacuum for an additional five minutes and examined for the formation of micropores. Following this, it is subjected to vacuum for 17 additional minutes, making a total time under vacuum of 30 minutes. Other than poking (with a specially-designed stainless steel poker 7 mm on one end and 4 mm on the other), the implants are not handled during the five and 17 minute vacuum periods.

The molds are then placed in a water bath at 37° C., connected to a lyophilizer at high vacuum (approximately 10 microbars) for two hours. The entire molds are then removed from the water bath. Compressive pressure is then applied. For instance, in a preferred embodiment, the mold lids are secured with washers and wing nuts, and five stainless steel needles or pins are placed into the implants as mandated by holes drilled in the mold surface. The mold and implants are placed into the lyophilizer for approximately 20 hours under high vacuum at room temperature. After removal from vacuum, the implants are removed from the molds. They should have a diameter of 7 mm and a height of 5 mm. They are placed in a petri dish taped closed in an oven at 47° C. for 24 hours. Following this they are stored under vacuum in the lyophilizer at −51° C.

The cartilage phase of the goat implant is then prepared. The cartilage phase is designed to incorporate the bioactive agent. The cartilage phase is 2 mm thick and is attached to the 5mm bone phase after the bone phase has been heated and cooled. No chemicals are used to stick one phase to the other. The same PLG is used to make the cartilage phase of the implants; however TGF-β is added only to this second phase. TGF-$β_1$ is a stable, multifunctional polypeptide growth factor and is stimulatory for cells of mesenchymal origin. The purity is greater than 97% as determined by SDS-PAGE, visualized by silver stain. The endotoxin level is determined to be less than 0.1 ng per 1 microgram of the cytokine.

The TGF-$β_1$ solution is prepared by reconstituting 2 micrograms thereof in 0.2 mL sterile filtered glass-distilled ultrapure water. All materials are handled under a hood. This will provide 180 ng TGF-$β_1$ per implant.

The same procedure is followed as in preparing the bone phase, using 0.36 g PGA:PLA to make the cartilage phase for twelve 7 mm×7 mm implants. A 25 mL Teflon beaker may be used to solubilize the polymer. The solution may require 30 minutes of stirring because of the smaller amount. It is important to make sure the polymer is well-solubilized. The TGF-$β_1$ solution is added by pipetting into the polymer/acetone solution and the mixture stirred for 3–5 minutes on the stirring machine. The polymer is then precipitated with ethyl alcohol as with the bone phase. The polymer is treated under vacuum in the Nalgene desiccator as for the bone phase, except that the polymer is rolled after 2 minutes of vacuum, rolled again after two more minutes of vacuum, and again after an additional two minutes of vacuum.

The bone phases are retrieved from the lyophilizer and placed into molds, rotated 180°, allowing the cartilage phase to be attached to what had been the bottom. The cartilage polymer is divided into twelve portions, placed into the molds on top of the bone phases and poked into place. The molds are vacuumed three minutes, and viewed under magnification, then poked again. This procedure is repeated with 4 additional minutes of vacuum, followed by 17 minutes of vacuum, for a total of 30 minutes under vacuum.

The molds are then subjected to high vacuum in the lyophilizer at 37° C. for four hours, pierced with five needles (or tines) per implant and placed into the lyophilizer for approximately 20 hours under high vacuum at room temperature. The completed implants are removed from the molds and stored in petri dishes placed closed under vacuum lyophilization at −51° C.

We claim:

1. An implant material comprising a biodegradable, porous and polymeric material having a pore size between about 50 μm and about 200 μm, and at least about 50% by volume porosity, the implant material comprising a bioactive agent substantially uniformly incorporated therein such that, when the implant material is used in an in vivo environment, the implant material provides a substantially smooth continuous release of the bioactive agent during the first two weeks of use.

2. The polymeric implant material of claim 1 wherein the percentage degradation of the polymeric implant material is greater than the percentage release of the bioactive agent during the first two weeks of use.

3. The polymeric implant material of claim 2 wherein less than about 25% of the bioactive agent is released during the first two weeks of use.

4. The polymeric implant material of claim 2 wherein less than about 10% of the bioactive agent is released during the first two weeks of use.

5. The polymeric implant material of claim 2 wherein the average molecular weight of the implant is reduced by at least about 30% during the first two weeks of use.

6. The polymeric implant material of claim 2 wherein the average molecular weight of the implant is reduced by at least about 30% during the first two weeks of use, and less than about 10% of the bioactive agent is released during the first two weeks of use.

7. The polymeric implant material of claim 1 wherein the surface axial strain of the polymeric implant material after four weeks of use is greater than the surface axial strain of the polymeric implant material before use.

8. The polymeric implant material of claim 1 wherein the surface axial strain of the polymeric implant material after four weeks of use is greater than the surface axial strain of the polymeric implant material before use, and less than about 10% of the bioactive agent is released during the first two weeks of use.

9. The polymeric implant material of claim 1 wherein the polymeric implant material has a substantially uniform composition.

10. The polymeric implant material of claim 1 wherein the bioactive agent is adapted to be smoothly released during the first eight weeks of use.

11. The polymeric implant material of claim 1 wherein the bioactive agent is released such that a graph of cumulative release of the bioactive agent versus time depicts a substantially sigmoidal curve.

12. The polymeric implant material of claim 1 wherein the bioactive agent is hydrophobic.

13. The polymeric implant material of claim 1 wherein the bioactive agent is a polypeptide.

14. The polymeric implant material of claim 1 wherein the bioactive agent is an enzyme.

15. The polymeric implant material of claim 1 wherein the bioactive agent is a cytokine.

16. The polymeric implant material of claim 1 wherein the bioactive agent is a growth factor.

17. The polymeric implant material of claim 1 wherein the bioactive agent comprises transforming growth factor-β (TGF-β).

18. The polymeric implant material of claim 16 wherein the growth factor is selected from the group consisting of platelet-derived growth factor (PDGF), epidermal growth factor (EGF), insulin-like growth factor-1 (IGF-1), basic fibroblast growth factor (bFGF), thyroid-derived chondrocyte stimulating factor (TDCSF), and bone morphogenic protein (BMP).

19. The polymeric implant material of claim 1 wherein the polymer is a copolymer of PLA and PGA.

20. The polymeric implant material of claim 19 wherein the copolymer is a 50:50 copolymer of PLA and PGA.

21. The polymeric implant material of claim 19 wherein the copolymer has an average molecular weight between about 10 kD and about 100 kD prior to use.

22. The polymeric material of claim 19 wherein the copolymer has an average molecular weight between about 40 kD and about 70 kD.

23. The polymeric implant material of claim 1 wherein the polymeric implant material has stress properties which are substantially comparable to the stress properties of cartilage.

24. The polymeric implant material of claim 1 wherein the polymeric implant material has compressibility properties which are substantially comparable to the compressibility properties of cartilage.

25. The polymeric implant material of claim 1 wherein the polymeric implant material has a porosity which is substantially comparable to the porosity of cartilage.

26. The polymeric implant material of claim 1 wherein the polymeric implant material has stress properties which are substantially comparable to the stress properties of bone.

27. The polymeric implant material of claim 1 wherein the polymeric implant material has compressibility properties which are substantially comparable to the compressibility properties of bone.

28. The polymeric implant material of claim 1 wherein the polymeric implant material has a porosity which is substantially comparable to the porosity of bone.

29. An implant material comprising a biodegradable, porous and polymeric material, the implant material comprising a bioactive agent substantially uniformly incorporated therein such that, when the implant material is used in an in vivo environment, the implant material provides a substantially smooth continuous release of the bioactive agent during the first two weeks of use, said implant material further comprising serum albumin present at less than about 100 μg per μg bioactive agent.

30. The polymeric implant material of claim 1 wherein the structure is adapted to release the bioactive agent during use over a period of at least about six weeks.

31. The polymeric implant material of claim 1 comprising between about 0.01 ng and about 1 mg of bioactive agent per milliliter of polymeric implant material.

32. The polymeric implant material of claim 1 comprising a plurality of passages having a diameter between about 1.0 mm and about 2.0 mm.

33. The polymeric implant material of claim 1 wherein the polymeric implant material is adapted to initially release the bioactive agent such that sufficient bioactive agent is present to promote migration of mesenchymal cells into the polymeric implant material without causing substantial differentiation of chondrocyte cells.

34. The polymeric implant material of claim 33 wherein the polymeric implant material is adapted such that after the initial release the material releases sufficient bioactive agent to promote differentiation of cells within the polymeric implant material.

35. The polymeric implant material of claim 1 comprising a plurality of bioactive agents, the bioactive agents being adapted to release in different amounts at different time periods.

36. A two-phase layered biodegradable implant, each layer comprising a biodegradable polymeric implant material of claim 1, wherein the first layer has stress properties substantially comparable to the stress properties of cartilage and wherein the second layer has stress properties substantially comparable to the stress properties of bone.

* * * * *

UNITED STATES PATENT AND TRADEMARK OFFICE
CERTIFICATE OF CORRECTION

PATENT NO. : 6,013,853

DATED : January 11, 2000

INVENTOR(S) : Athanasiou et al.

It is certified that error appears in the above-identified patent and that said Letters Patent is hereby corrected as shown below:

At column 12, line 32, please delete "14" and replace with --12--.

At column 12, line 33, please delete "12" and replace with --14--.

Signed and Sealed this

Tenth Day of October, 2000

Attest:

Q. TODD DICKINSON

*Attesting Officer*    *Director of Patents and Trademarks*